(12) United States Patent
Ghatnekar et al.

(10) Patent No.: US 8,476,221 B2
(45) Date of Patent: Jul. 2, 2013

(54) METHODS AND COMPOSITIONS FOR THE TREATMENT OF METABOLIC DISORDERS

(75) Inventors: Gautam S. Ghatnekar, Charleston, SC (US); Justin Brower, Cary, NC (US)

(73) Assignee: Halimed Pharmaceuticals, Inc., Charleston, SC (US)

( * ) Notice: Subject to any disclaimer, the term of this patent is extended or adjusted under 35 U.S.C. 154(b) by 0 days.

(21) Appl. No.: 13/423,491

(22) Filed: Mar. 19, 2012

(65) Prior Publication Data

US 2012/0238490 A1  Sep. 20, 2012

Related U.S. Application Data

(60) Provisional application No. 61/454,360, filed on Mar. 18, 2011, provisional application No. 61/454,365, filed on Mar. 18, 2011.

(51) Int. Cl.
*A61K 38/00* (2006.01)
*A61P 9/10* (2006.01)
*C07K 14/47* (2006.01)

(52) U.S. Cl.
USPC .............................. 514/1.9; 514/6.9; 514/7.4

(58) Field of Classification Search
None
See application file for complete search history.

(56) References Cited

U.S. PATENT DOCUMENTS

| | | | |
|---|---|---|---|
| 4,160,452 A | 7/1979 | Theeuwes |
| 4,256,108 A | 3/1981 | Theeuwes |
| 4,265,874 A | 5/1981 | Bonsen et al. |
| 4,883,666 A | 11/1989 | Sabel et al. |
| 5,007,790 A | 4/1991 | Shell |
| 5,114,719 A | 5/1992 | Sabel et al. |
| 5,582,837 A | 12/1996 | Shell |
| 5,601,835 A | 2/1997 | Sabel et al. |
| 5,972,389 A | 10/1999 | Shell et al. |
| 6,039,967 A | 3/2000 | Ottoboni et al. |
| 6,086,909 A | 7/2000 | Harrison et al. |
| 6,172,062 B1 | 1/2001 | Clark et al. |
| 6,207,180 B1 | 3/2001 | Ottoboni et al. |
| 6,258,819 B1 | 7/2001 | Clark et al. |
| 6,340,475 B2 | 1/2002 | Shell et al. |
| 6,355,641 B1 | 3/2002 | Coffen et al. |
| 6,376,500 B2 | 4/2002 | Clark et al. |
| 6,416,779 B1 | 7/2002 | D'Augustine et al. |
| 6,417,186 B1 | 7/2002 | Jahangir |
| 6,451,808 B1 | 9/2002 | Cowles |
| 6,488,962 B1 | 12/2002 | Berner et al. |
| 6,500,822 B2 | 12/2002 | Weikert et al. |
| 6,515,198 B2 | 2/2003 | Cockayne et al. |
| 2002/0051820 A1 | 5/2002 | Shell et al. |
| 2003/0039688 A1 | 2/2003 | Shell et al. |
| 2003/0044466 A1 | 3/2003 | Markey et al. |
| 2003/0104053 A1 | 6/2003 | Gusler et al. |
| 2003/0104062 A1 | 6/2003 | Berner et al. |
| 2003/0147952 A1 | 8/2003 | Lim et al. |
| 2008/0139481 A1 | 6/2008 | Dix |
| 2008/0234202 A1 | 9/2008 | Brower et al. |
| 2010/0130432 A1 | 5/2010 | Brower et al. |

FOREIGN PATENT DOCUMENTS

| | | |
|---|---|---|
| WO | WO 2009/011757 A1 | 10/1990 |
| WO | WO 93/18755 A1 | 9/1993 |
| WO | WO 97/47285 A1 | 12/1997 |
| WO | WO 98/11879 A1 | 3/1998 |
| WO | WO 98/55107 A1 | 12/1998 |
| WO | WO 01/32217 A2 | 5/2001 |
| WO | WO 01/56544 A2 | 8/2001 |
| WO | WO 01/97783 A1 | 12/2001 |
| WO | WO 02/32416 A2 | 4/2002 |
| WO | WO 02/096404 A1 | 12/2002 |
| WO | WO 03/035029 A1 | 5/2003 |
| WO | WO 03/035039 A1 | 5/2003 |
| WO | WO 03/035040 A1 | 5/2003 |
| WO | WO 03/035041 A1 | 5/2003 |
| WO | WO 03/035177 A2 | 5/2003 |
| WO | WO 2010085661 A1 * | 7/2010 |

OTHER PUBLICATIONS

Feifel et al. "The Acute and Subchronic Effects of a Brain-penetrating, Neurotensin-1 Receptor Agonist on Feeding, Body Weight and Temperature" Jan. 2010, *Neuropharmacology* 58(1):195-198.

Taylor-McMahon et al. "Highly Potent Neurotensin Analog that Causes Hypothermia and Antinociception" Feb. 25, 2000 *Eur. J. Pharmacol.* 390(1-2):107-111.

Taylor-McMahon et al. "Neurotensin: Peptide for the Next Millennium" Sep. 25, 2000, *Regulatory Peptides* 93(1-3):125-136.

* cited by examiner

*Primary Examiner* — Cecilia J Tsang
*Assistant Examiner* — Zachary J Miknis
(74) *Attorney, Agent, or Firm* — Pepper Hamilton LLP

(57) ABSTRACT

Embodiments described herein are directed to methods for the treatment and control of hyperlipidemia, hypercholesterolemia, dyslipidemia, and other lipid disorders, and in delaying the onset of or reducing the risk of conditions and sequelae that are associated with these diseases, including atherosclerosis and non-insulin dependent diabetes. In addition, embodiments are directed to methods of treating coronary heart disease and metabolic syndrome. Embodiments are also directed to neurotensin analogs. In embodiments, the neurotensin analogs may be capable of binding to neurotensin receptors and, upon binding, may modulate the levels of lipids in subjects.

3 Claims, 3 Drawing Sheets

FORMULA I

HPI-234

HPI-244

HPI-262

HPI-263

HPI-363

HPI-501

METHODS AND COMPOSITIONS FOR THE TREATMENT OF METABOLIC DISORDERS

CROSS-REFERENCE TO RELATED APPLICATIONS

This application claims benefit of priority to U.S. Provisional Patent Application No. 61/454,360 and No. 61/454,365 filed on Mar. 18, 2011 entitled "Methods and Compositions for the Treatment of Metabolic Disorders," the entire contents of which are hereby incorporated by reference.

GOVERNMENT INTERESTS

Not applicable

PARTIES TO A JOINT AGREEMENT

Not applicable

INCORPORATION BY REFERENCE OF MATERIAL SUBMITTED ON A COMPACT DISC

Not applicable.

BACKGROUND

Not applicable.

SUMMARY

Embodiments described herein are directed towards methods, devices, compositions and kits for the treatment of metabolic disorders. Embodiments herein are directed to a method of treatment of hyperlipidemia, hypercholesterolemia, dyslipidemia, other lipid disorders and other conditions and sequelae that are associated with these diseases such as, without limitation, atherosclerosis and non-insulin dependent diabetes (i.e., type 2 diabetes).

Embodiments include a pharmaceutical composition comprising a compound according to Formula I and a pharmaceutically acceptable excipient. In embodiments, the compound is a neurotensin analog. In some embodiments, the compound may be

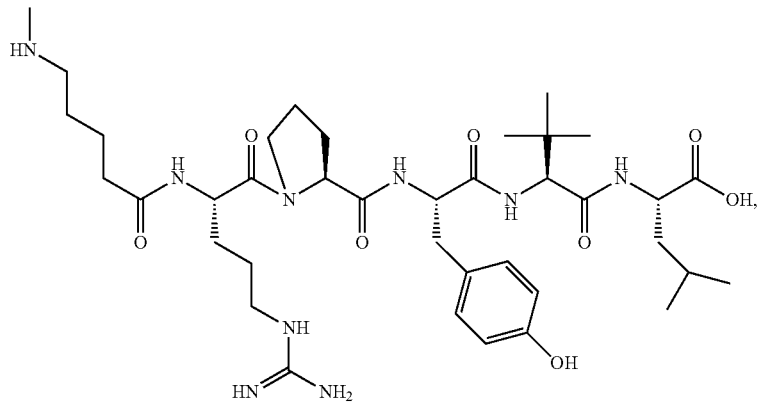

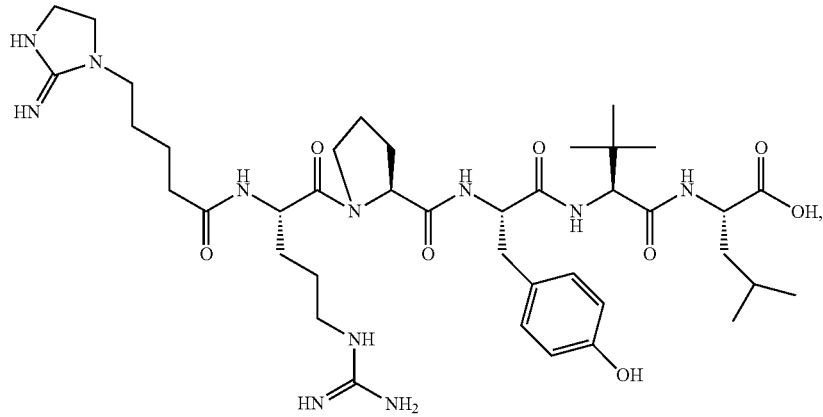

HPI-262
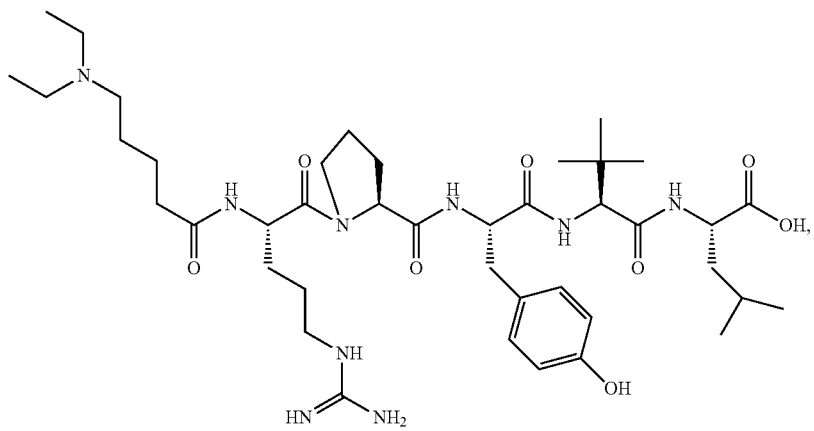
HPI-263
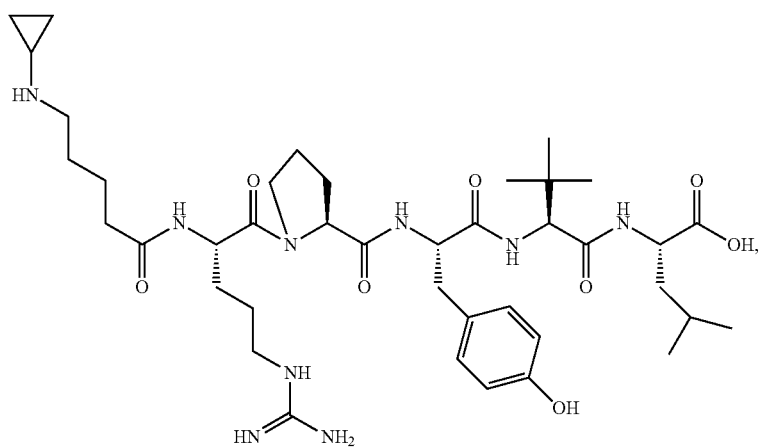
HPI-363
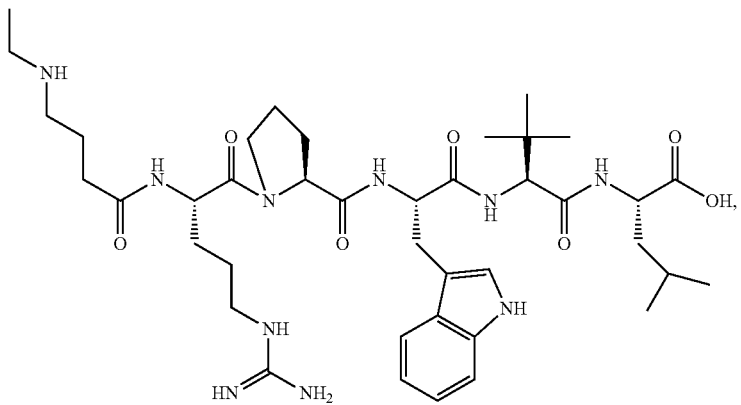

HPI-501

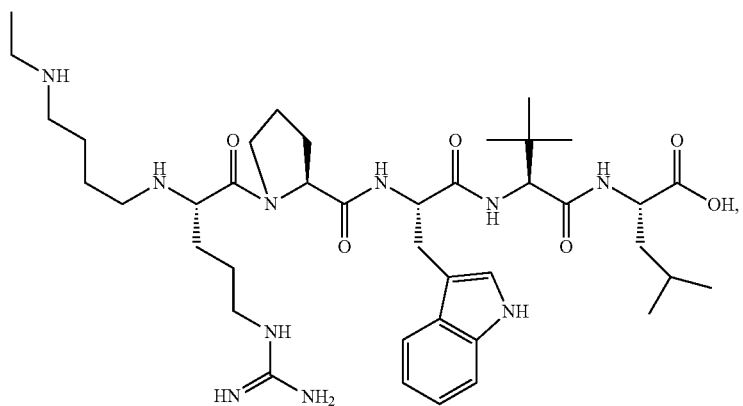

or a combination thereof. In some embodiments, the compound may be present in the pharmaceutical composition in a therapeutically effective amount.

Embodiments describe a method of treating a lipid disorder comprising administering a compound according to Formula I. In embodiments, the compound may be a neurotensin analog. In some embodiments, the compound may be

HPI-234

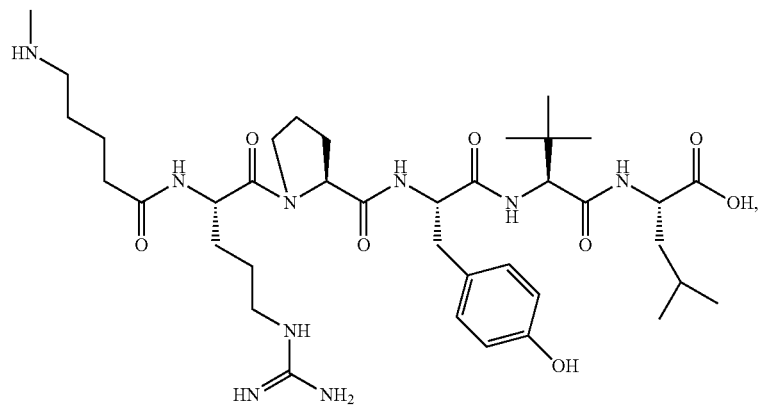

HPI-244

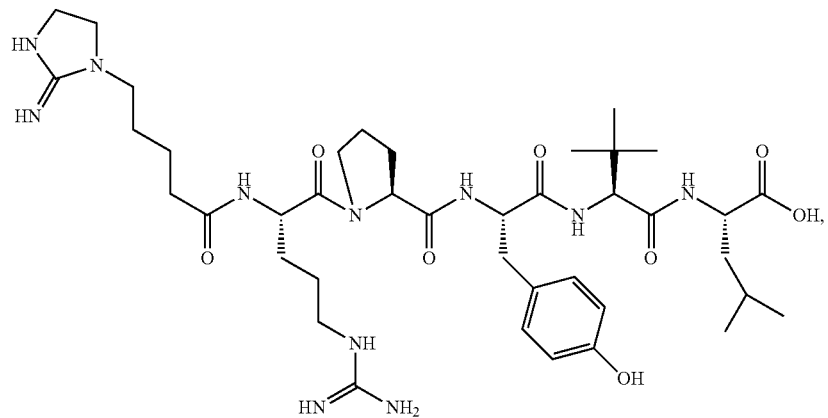

HPI-262

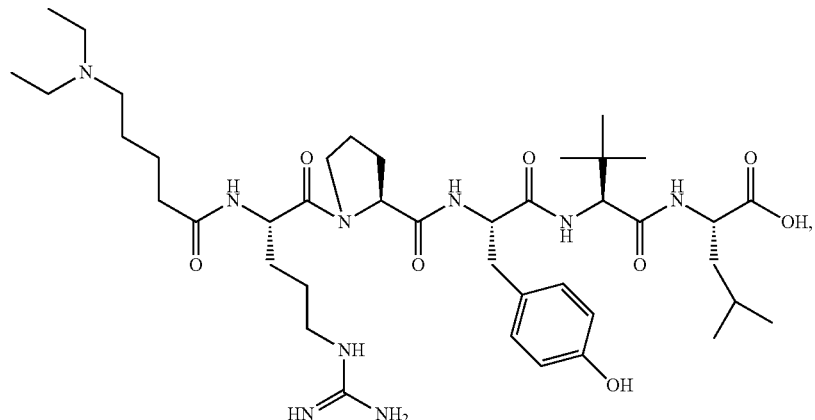

HPI-263

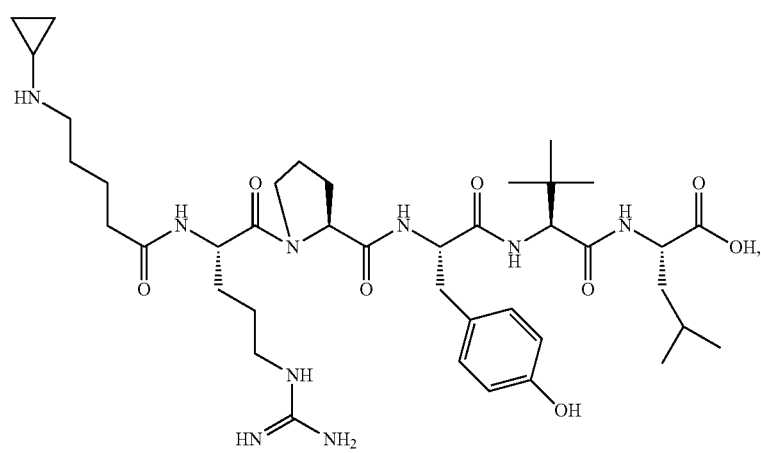

HPI-363

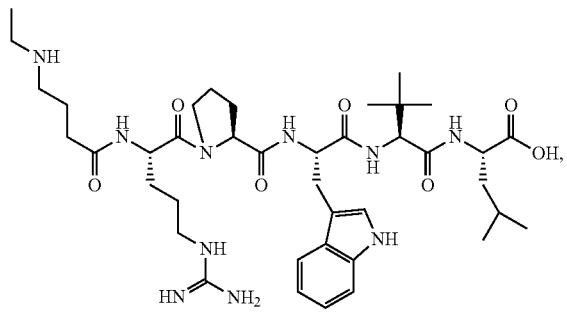

HPI-501

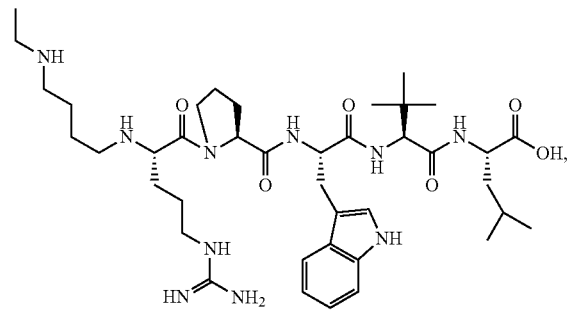

or a combination thereof. In some embodiments, the compound may in a pharmaceutical composition, which may further comprise a pharmaceutically acceptable excipient. In some embodiments, the compound may be present in the pharmaceutical composition in a therapeutically effective amount. In some embodiments, the lipid disorder is selected from hyperlipidemia, dyslipidemia, hypercholesterolemia, hypertrigyceridemia, hyperglycemia, obesity or a combination thereof.

Embodiments describe a method of treating non-insulin dependent diabetes mellitus comprising administering a pharmaceutical composition comprising a compound according to Formula I. In embodiments, the compound may be a neurotensin analog. In some embodiments, the compound may be HPI-234
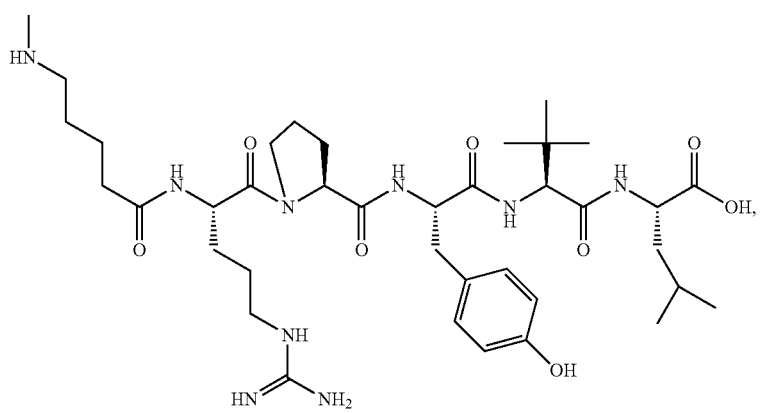
HPI-244
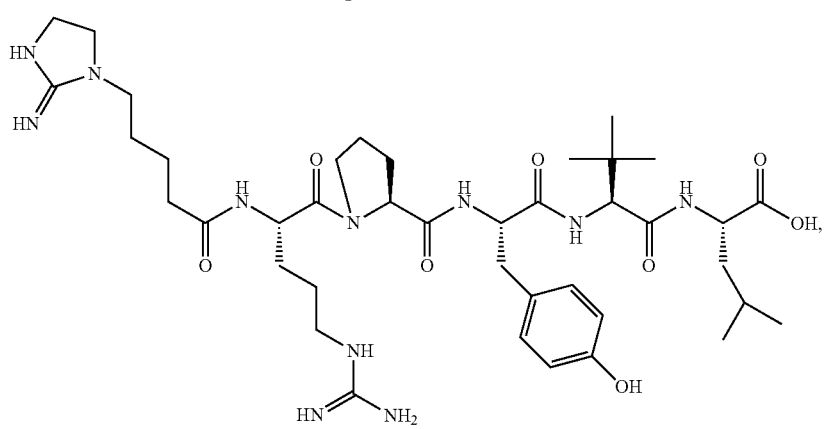
HPI-262
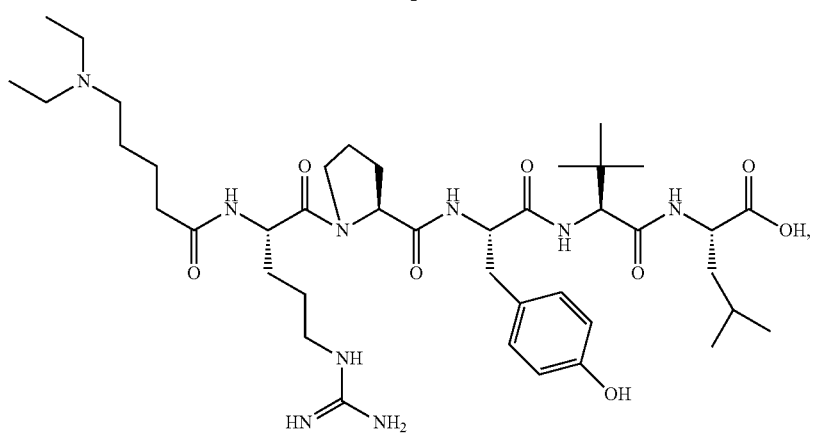
HPI-263
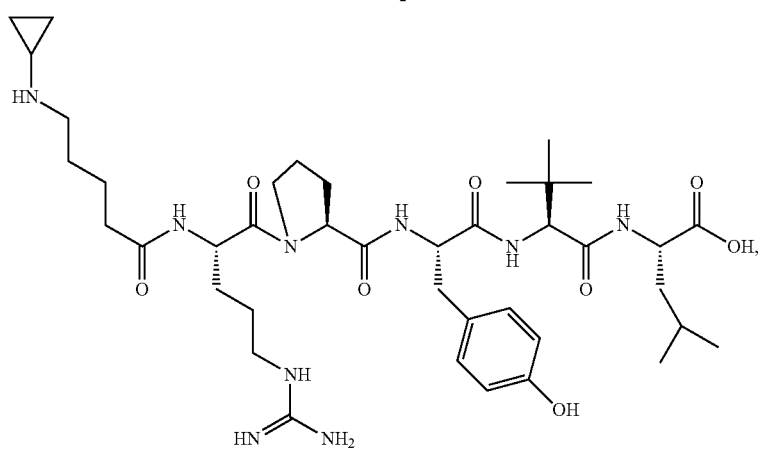

-continued

HPI-363

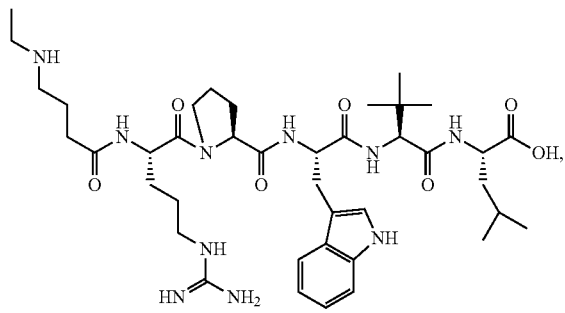

HPI-501

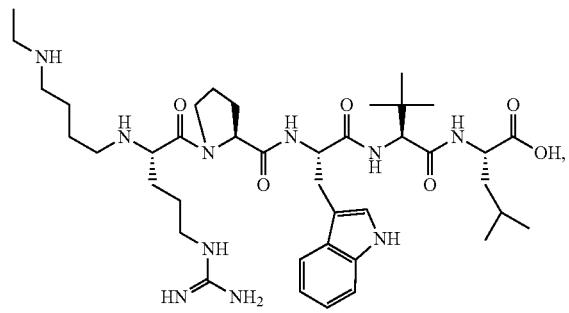

or a combination thereof. In some embodiments, the compound may be present in a therapeutically effective amount.

Embodiments describe a method of treating conditions associated with non-insulin dependent diabetes mellitus comprising administering a pharmaceutical composition comprising a compound according to Formula I. In embodiments, the compound may be a neurotensin analog. In some embodiments, the compound may be

HPI-234

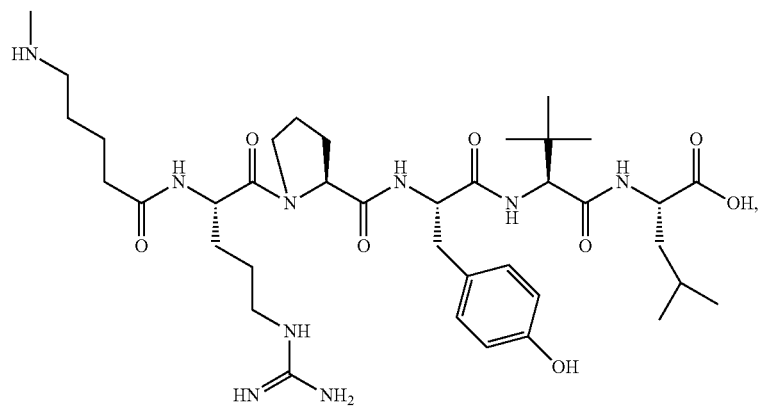

HPI-244

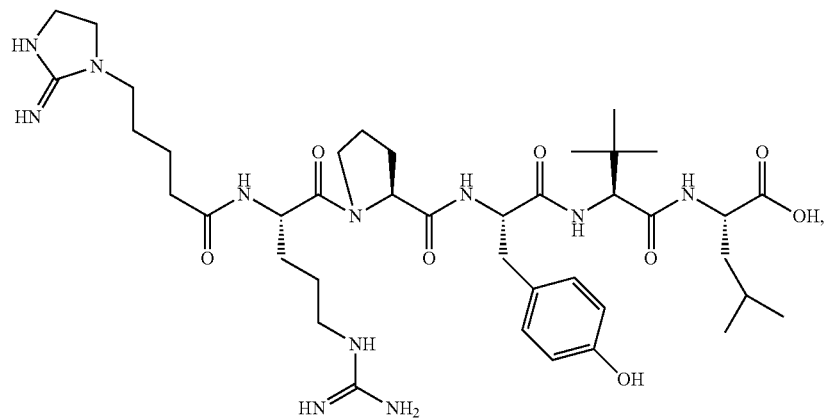

-continued

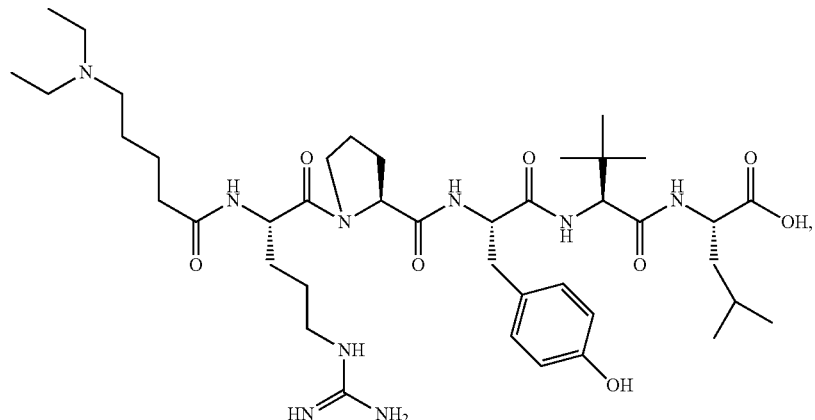

HPI-262

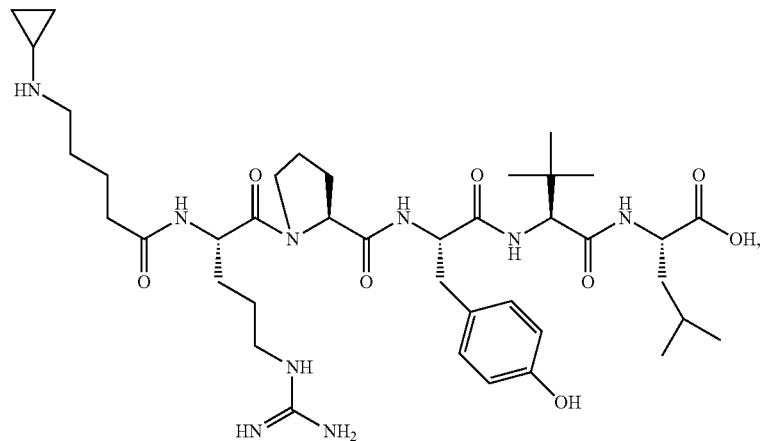

HPI-263

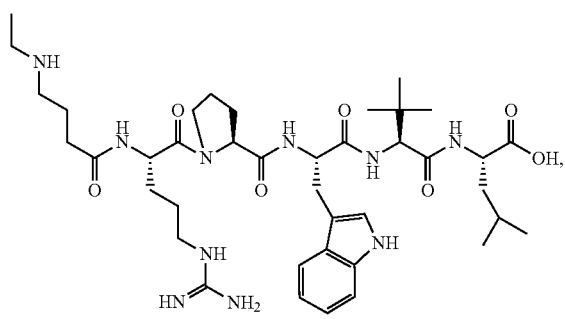

HPI-363

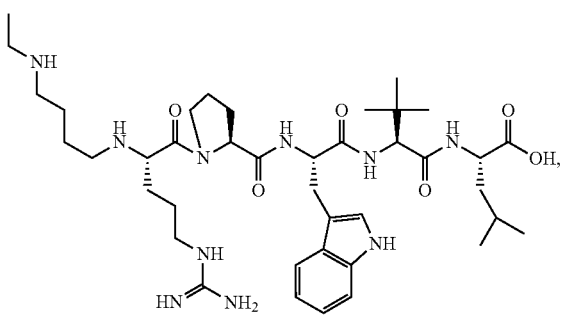

HPI-501 or a combination thereof. In some embodiments, the compound may be present in a therapeutically effective amount. In some embodiments, the condition associated with non-insulin dependent diabetes mellitus may be selected from hyperlipidemia, dyslipidemia, hypercholesterolemia, hypertriglyceridemia, hyperglycemia, obesity or a combination thereof. In some embodiments, the condition associated with non-insulin dependent diabetes mellitus may be selected from atherosclerosis or hyperinsulinemia. In some embodiments, the condition associated with non-insulin dependent diabetes mellitus is selected from cardiovascular disease or metabolic syndrome.

In some embodiments, a method of treating or normalizing abnormal lipid concentrations in a subject comprises administering a compound including the structure of Formula I to a subject in need thereof. See FIG. 1. In some embodiments, the abnormal lipid concentration may be selected from total lipid concentration, total cholesterol concentration, total apolipoprotein concentration, total lipoprotein concentration, LDL concentration, VLDL concentration, IDL concentration, HDL concentration, HDL-cholesterol concentration, LDL-cholesterol concentration, triglycerides, or a combination thereof. In some embodiments, a method of reducing levels of lipids comprises administering a compound including the structure of Formula I to a subject in need thereof. In some embodiments, the level of lipids may be lowered in subjects with abnormal lipid levels. In some embodiments, the level of lipids may be lowered in subjects with abnormally high lipid levels. In some embodiments, the level of lipids may be lowered in subjects with abnormally low lipid levels. In some embodiments, the level of lipids may be reduced in subjects with normal lipid levels. In some embodiments, the level of lipids comprises the level of cholesterol, triglycerides or a combination thereof. In some embodiments, a method of lowering lipid concentrations comprises administering a compound including the structure of Formula I to a subject in need thereof. In some embodiments, the lipid concentration may be selected from total lipid concentration, total cholesterol concentration, total apolipoprotein concentration, total lipoprotein concentration, LDL concentration, VLDL concentration, IDL concentration, LDL-cholesterol concentration, triglycerides, or a combination thereof. In some embodiments, a method of increasing the ratio of HDL concentration to LDL concentration comprises administering a compound including the structure of Formula I to a subject in need thereof. In some embodiments, the HDL concentration is the concentration of HDL-cholesterol. In some embodiments, the LDL concentration is the concentration of LDL-cholesterol. In some embodiments, a method of increasing HDL concentration comprises administering a compound including the structure of Formula I to a subject in need thereof. In some embodiments, the HDL concentration is the concentration of HDL-cholesterol. In some embodiments, the total lipid concentration comprises the sum of cholesterol and triglyceride concentrations. In some embodiments, the total cholesterol concentration comprises the sum of HDL-cholesterol and LDL-cholesterol concentrations. In some embodiments, the total apolipoprotein concentration comprises the sum of the concentrations of apolipoproteins A, B, C, and E. In some embodiments, the total lipoprotein concentration comprises the sum of the concentrations of HDL, LDL, VLDL and IDL.

Embodiments describe a compound having the formula:

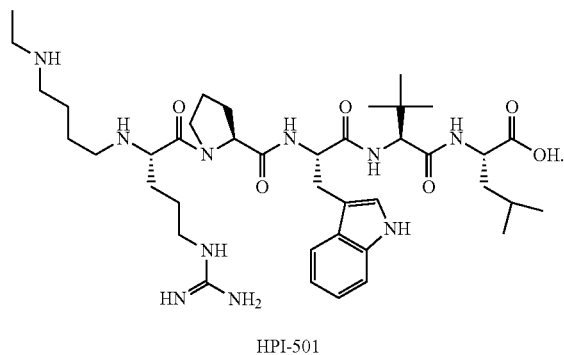 [SMILES: CCNCCCCN[C@@H](CCCNC(=N)N)C(=O)N1CCC[C@H]1C(=O)N[C@@H](Cc1c[nH]c2ccccc12)C(=O)N[C@H](C(=O)N[C@@H](CC(C)C)C(=O)O)C(C)(C)C]

HPI-501

DESCRIPTION OF DRAWINGS

For a fuller understanding of the nature and advantages of the present invention, reference should be had to the following detailed description taken in connection with the accompanying drawings, in which.

DETAILED DESCRIPTION

Figure 1:
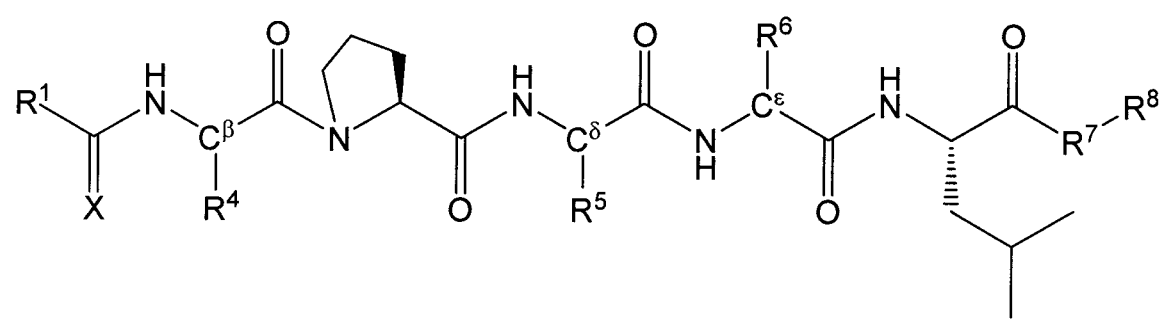
FIG. 1 illustrates the chemical structure of the compounds of Formula I of the invention.

Before the present compositions and methods are described, it is to be understood that this invention is not limited to the particular processes, compositions, or methodologies described, as these may vary. The terminology used in the description is for the purpose of describing the particular versions or embodiments only, and it is not intended to limit the scope of the present invention which will be limited only by the appended claims. Unless defined otherwise, all technical and scientific terms used herein have the same meanings as commonly understood by one of ordinary skill in the art. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a", "an", and "the" include plural reference unless the context clearly dictates otherwise. Thus, for example, reference to an "element" is a reference to one or more elements and equivalents thereof known to those skilled in the art, and so forth.

As used herein, the term "about" means plus or minus 10% of the numerical value of the number with which it is being used. Therefore, about 50% means in the range of 45%-55%.

A "subject" or a "mammal" includes a human or a non-human mammal. Non-human mammals include, but are not limited to, livestock and pets, such as ovine, bovine, porcine, canine, feline and marine mammals. Preferably, the subject or mammal is human.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", when used in conjunction with a neurotensin analog, can include, but is not limited to, providing the neurotensin analog into or onto the target tissue; providing the neurotensin analog systemically to a patient by, e.g., intravenous injection whereby the therapeutic reaches the target tissue; providing the neurotensin analog in the form of the encoding sequence thereof to the target tissue (e.g., by so-called gene-therapy techniques). "Administering" a composition may be accomplished by oral, injection, topical administration, or by any method in combination with other known techniques.

The term "improves" is used to convey that the present invention changes either the appearance, form, characteristics and/or the physical attributes of the tissue to which it is being provided, applied or administered. The change in form may be demonstrated by any of the following alone or in combination: prevention of or reduction in symptoms of hyperlipidemia, hypercholesterolemia, dyslipidemia, and other lipid disorders; delaying the onset of or reducing the risk of conditions and sequelae that are associated with such diseases; delaying the onset of atherosclerosis or non-insulin dependent diabetes; reduction in levels of total cholesterol or Low Density Lipoprotein (LDL) cholesterol; reduction in levels of small dense LDL-cholesterol particles, Very Low Density Lipoproteins (VLDL) or Intermediate Density Lipoproteins (IDL); increased levels of High Density Lipoprotein (HDL) cholesterol; lowered risk of coronary heart disease; reduction in level of triglycerides; reduction in symptoms of or prevention of obesity, hypertension, diabetes, insulin resistance, glucose intolerance, cardiovascular disease, pancreatitis and prothrombotic state; reduction in food intake; and control of appetite.

The term "inhibiting" includes the administration of a compound of the present invention to prevent the onset of the symptoms, alleviating the symptoms, or eliminating the disease, condition or disorder.

As used herein, the term "therapeutic" means an agent utilized to treat, combat, ameliorate, prevent or improve an unwanted condition or disease of a patient. In part, embodiments of the present invention are directed to the treatment of lipid disorders or stabilization of abnormal lipid levels.

As used herein, the phrase "effective amount" or "therapeutically effective amount" refers to a nontoxic but sufficient amount of the composition used in the practice of the invention that is effective to achieve the desired effect, i.e., to treat lipid disorders in a mammal. The activity contemplated by the present methods includes both medical therapeutic and/or prophylactic treatment, as appropriate, including, for example, a reduction and/or alleviation of the signs, symptoms, or causes of a disease or disorder, or any other desired alteration of a biological system. The specific dose of a compound administered according to this invention to obtain therapeutic and/or prophylactic effects will, of course, be determined by the particular circumstances surrounding the case, including, for example, the compound administered, the route of administration, and the condition being treated. A therapeutically effective amount of compound of this invention is typically an amount such that when it is administered in a physiologically tolerable excipient composition, it is sufficient to achieve an effective systemic concentration or local concentration in the tissue. The compounds are effective over a wide dosage range. For example, suitable doses of compounds of the invention to be administered may be from about 0.01 mg/kg to about 300 mg/kg body weight. In some embodiments, dosages are from about 1 mg/kg to about 100 mg/kg body weight. However, it will be understood that the effective amount administered will be determined by the physician in the light of the relevant circumstances including the condition to be treated, the choice of compound to be administered, and the chosen route of administration, and therefore the above dosage ranges are not intended to limit the scope of this disclosure in any way.

The terms "treat," "treated," or "treating" as used herein refers to both therapeutic treatment and prophylactic or preventative measures, wherein the object is to prevent, ameliorate the effects of or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; reducing the severity of a symptom of a condition, disease or disorder; reducing the frequency of a symptom of a condition, disease or disorder; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

The term "alkyl," as used herein, refers to a branched or unbranched saturated hydrocarbon group of 1 to 24 carbon atoms, such as, without limitation, methyl, ethyl, n-propyl, isopropyl, n-butyl, isobutyl, tert-butyl, pentyl, hexyl, heptyl, octyl, decyl and the like. Preferred alkyl groups herein contain 1 to 6 carbon atoms. Alkyl groups may be optionally substituted with one to three groups chosen from halo, amino, methoxy, ethoxy, hydroxyl, methylthio, methylsulfonyl, nitro, aryl, heterocyclyl and heteroaryl.

The term "alkenyl," as used herein, refers to a branched or unbranched hydrocarbon group of 1 to 24 carbon atoms containing at least one unsaturated bond, such as, without limitation, vinyl, propenyl, butenyl, pentenyl, hexenyl, heptenyl, octenyl, decenyl, and the like. Preferred alkyl groups herein contain 1 to 6 carbon atoms. Alkyl groups may be optionally substituted with one to three groups chosen from halo, amino, methoxy, ethoxy, hydroxyl, methylthio, methylsulfonyl, nitro, aryl, heterocyclyl and heteroaryl.

The term "cycloalkyl" refers to ring-containing alkyl radicals. Examples include cyclohexyl, cyclopentyl, cyclopropyl, cyclopropylmethyl and norbornyl. Cycloalkyl groups may be optionally substituted with one to three groups chosen from halo, amino, methoxy, ethoxy, hydroxyl, methylthio, methylsulfonyl, nitro, aryl, heterocyclyl and heteroaryl.

The term "aryl," employed alone or in combination with other terms, means, unless otherwise stated, a carbocyclic aromatic group containing one or more rings (typically one, two or three rings). Multiple rings may be attached together in a pendent manner, such as a biphenyl, or may be fused, such as naphthalene. Examples include, but are not limited to, phenyl, anthracyl and naphthyl. Preferred are phenyl and naphthyl, most preferred is phenyl. Aryl groups may be optionally substituted with one to three groups chosen from halo, amino, methoxy, ethoxy, hydroxyl, methylthio, methylsulfonyl, nitro, aryl, heterocyclyl and heteroaryl.

The term "heterocycle", "heterocyclyl" or "heterocyclic" by itself or as part of another substituent means, unless otherwise stated, an unsubstituted or substituted, stable, mono- or multicyclic heterocyclic ring system consisting of carbon atoms and at least one heteroatom selected from the group consisting of N, O, and S, and wherein the nitrogen and sulfur heteroatoms may be optionally oxidized, and the nitrogen atom may be optionally quaternized. The heterocycle may be attached to the compound of which it is a component, unless otherwise stated, at any heteroatom or carbon atom in the heterocycle that affords a stable structure. Heterocyclic groups may be optionally substituted with one to three groups chosen from halo, amino, methoxy, ethoxy, hydroxyl, methylthio, methylsulfonyl, nitro, aryl, heterocyclyl and heteroaryl.

Examples of non-aromatic heterocycles include monocyclic groups such as: aziridinyl, oxiranyl, thiiranyl, azetidinyl, oxetanyl, thietanyl, imidazolinyl, pyrazolidinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydropyridinyl, 1,4-dihydropyridinyl, piperazinyl, morpholinyl, thiomorpholinyl, pyranyl, 2,3-dihydropyranyl, tetrahydropyranyl, 1,4-dioxanyl, 1,3-dioxanyl, homopiperazinyl, homopiperidinyl, 1,3-dioxepinyl, 4,7-dihydro-1,3-dioxepinyl and hexamethyleneoxide.

The term "heteroaryl" or "heteroaromatic" refers to a heterocycle having aromatic character. A monocyclic heteroaryl group is preferably a 5-, 6-, or 7-membered ring, examples of which are pyrrolyl, furyl, thienyl, pyridyl, pyrimidinyl and pyrazinyl. A polycyclic heteroaryl may comprise multiple aromatic rings or may include one or more partially saturated rings. Heteroaryl groups may be optionally substituted with one to three groups chosen from halo, amino, methoxy, ethoxy, hydroxyl, methylthio, methylsulfonyl, nitro, aryl, heterocyclyl and heteroaryl.

Examples of monocyclic heteroaryl groups include, for example, six-membered monocyclic aromatic rings such as, for example, pyridyl, pyrazinyl, pyrimidinyl and pyridazinyl; and five-membered monocyclic aromatic rings such as, for example, thienyl, furyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heteroaryl groups containing a partially saturated ring include tetrahydroquinolyl and 2,3-dihydrobenzofuryl.

Examples of polycyclic heteroaryls include indolyl, indolinyl, quinolyl, tetrahydroquinolyl, isoquinolyl, 1,2,3,4-tetrahydroisoquinolyl, cinnolinyl, quinoxalinyl, quinazolinyl, phthalazinyl, 1,8-naphthyridinyl, 1,4-benzodioxanyl, chromene-2-one-yl (coumarinyl), dihydrocoumarin, chromene-4-one-yl, benzofuryl, 1,5-naphthyridinyl, 2,3-dihydrobenzofuryl, 1,2-benzisoxazolyl, benzothienyl, benzoxazolyl, benzothiazolyl, purinyl, benzimidazolyl, benzotriazolyl, thioxanthinyl, benzazepinyl, benzodiazepinyl, carbazolyl, carbolinyl, acridinyl, pyrrolizidinyl and quinolizidinyl.

As used herein, the terms "peptide," "polypeptide," or "protein" are used interchangeably, and refer to a compound comprised of amino acid residues covalently linked by peptide bonds. A protein or peptide must contain at least two amino acids, and no limitation is placed on the maximum number of amino acids that can comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs and fusion proteins, among others. The polypeptides include natural peptides, recombinant peptides, synthetic peptides or a combination thereof. A peptide that is not cyclic will have a N-terminal and a C-terminal. The N-terminal will have an amino group, which may be free (i.e., as a NH2 group) or appropriately protected (for example, with a BOC or aFmoc group). The C-terminal will have a carboxylic group, which may be free (i.e., as a COOH group) or appropriately protected (for example, as a benzyl or a methyl ester). A cyclic peptide does not have free N- or C-terminal, since the ends are covalently bonded through an amide bond to form the cyclic structure. Amino acids may be represented by their full names (for example, leucine), 3-letter abbreviations (for example, Leu) and 1-letter abbreviations (for example, L). The structure of amino acids and their abbreviations can be found in the chemical literature, such as in Stryer, "Biochemistry", 3rd Ed., W. H. Freeman and Co., New York, 1988. As used herein, tLeu represents tert-leucine and Pro* represents hydroxyproline.

As used herein, the term "biologically active," with respect to the compounds described herein, means that the compounds elicit a biological response in a mammal, which can be monitored and characterized in comparison with an untreated mammal. One preferred biological response within the invention relates to the ability of the compound to induce changes in lipid concentrations of blood, plasma, serum, urine, saliva, body fluid, and interstitial fluid in a mammal. In this particular case, the compound may be administered to the subject, orally, nasally, rectally, intravaginally, parenterally, buccally, sublingually, intragastrically or topically.

"Medical intervention", as used herein, means a set of one or more medical procedures or treatments that are required for ameliorating the effects of, delaying, halting or reversing a disease or disorder of a subject. A medical intervention may involve surgical procedures or not, depending on the disease or disorder in question. A medical intervention may be wholly or partially performed by a medical specialist, or may be wholly or partially performed by the subject himself or herself, if capable, under the supervision of a medical specialist or according to literature or protocols provided by the medical specialist.

As used herein and unless otherwise indicated, the phrase "regulating metabolism" indicates an observable (i.e., measurable) change in at least one aspect of metabolism including, but not limited to, total blood lipid content, blood HDL cholesterol, blood LDL cholesterol, blood VLDL cholesterol, blood triglyceride, blood Lp(a), blood apo A-I, blood apo E or blood non-esterified fatty acids.

As used herein and unless otherwise indicated, the phrase "altering metabolism" indicates an observable (i.e., measurable) change in at least one aspect of metabolism including, but not limited to, total blood glucose content, blood insulin, the blood insulin to blood glucose ratio, insulin sensitivity, or oxygen consumption.

The term "synergistic", when applied to the use of two or more drugs in a therapeutic treatment, indicates that the therapeutic benefit obtained by combining the two or more drugs in a treatment is greater than the juxtaposition of the therapeutic benefit obtained when each drug is used by itself. If the first drug provides benefit "x" and the second drug provides benefit "y", the benefit provided by combining the two drugs has to be greater than "x+y" to characterize synergy or synergistic properties. Synergistic drugs may be administered concomitantly or sequentially, in the same formulation or different formulations.

"Pharmaceutically acceptable carrier" or "pharmaceutically acceptable excipient" means a pharmaceutically acceptable material, composition or carrier, such as a liquid or solid filler, diluent, excipient, solvent or encapsulating material, involved in carrying or transporting the compound(s) of the present invention within or to the subject such that the compound(s) can perform its intended function. Typically, such compounds are carried or transported from one organ, or portion of the body, to another organ, or portion of the body. Each carrier must be "acceptable" in the sense of being compatible with the other ingredients of the formulation, and not injurious to the patient. Some examples of materials that can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations or combinations thereof. As used herein "pharmaceutically acceptable carrier"

also includes any and all coatings, antibacterial and antifungal agents, and absorption delaying agents, and the like that are compatible with the activity of the compound, and are physiologically acceptable to the subject. Supplementary active compounds can also be incorporated into the compositions.

As used herein, the term "container" includes any receptacle for holding the pharmaceutical composition. For example, in one embodiment, the container is the packaging that contains the pharmaceutical composition. In other embodiments, the container is a receptacle other than the packaging that contains the pharmaceutical composition, i.e., the container is a receptacle, such as a box or vial that contains the packaged pharmaceutical composition or unpackaged pharmaceutical composition and the instructions for use of the pharmaceutical composition. Packaging techniques are well known in the art. The instructions for use of the pharmaceutical composition may, for example, be contained on the packaging containing the pharmaceutical composition, and as such the instructions form an increased functional relationship to the packaged product. In other embodiments, the instructions may contain information pertaining to the compound's ability to perform its intended function, e.g., treating, preventing, or reducing one or more lipoprotein abnormalities in a subject.

"Applicator," as the term is used herein, is used to identify any device including, but not limited to, a hypodermic syringe, a pipette, and the like, for administering the compounds and compositions used in the practice of the invention.

As used herein "controlled release" is meant the regulated spatial and temporal release of a compound from a formulation.

As used herein "delayed release" is meant that the therapeutically active component is not immediately released from the formulation (e.g., a carrier particle).

As used herein "pulmonary delivery" and "respiratory delivery" refer to delivery of a compound or analogs thereof to a subject by inhalation through the mouth and into the lungs.

As used herein "sustained release" is meant a form of controlled release whereby the therapeutically active compound is released over an extended period of time.

As used herein, "formulated for pulmonary administration" refers to a composition of the invention containing a therapeutically active compound and formulated with a pharmaceutically acceptable excipient to form a dispersible composition. Compositions formulated for pulmonary administration (e.g., as a liquid, aerosol, powder, and any other pulmonary formulation described herein) are those manufactured or sold in accordance with governmental regulations regarding a therapeutic regimen that includes instructions for the administration of the composition.

In some embodiments, the compounds are represented by the Formula I.

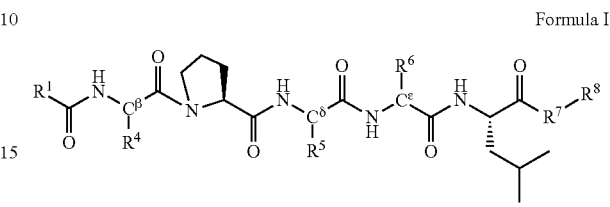

Formula I wherein:

$R^1$ is H, alkyl, cycloalkyl, aryl, heteroaryl, heterocyclic or —$C^{\alpha}HR^2R^3$;

$R^2$ and $R^4$ are independently H, —$(CH_2)_m NR^9 R^{10}$, —$(CH_2)_m N(CH_3)R^9 R^{10}$, —$(CH_2)_m NR^9 C(=NR^9)NR^9 R^{10}$, or —$(CH_2)_m$-imidazolidin-2-imin-1-yl;

$R^3$ is H, —$NR^9 R^{10}$, —$N(CH_3)R^9 R^{10}$, —$N(R^9)$—$C(=O)R^9$, —$C^{\Phi}HR^9 R^{10}$, —$C^{\Phi}H(R^9)$—$C(=O)R^{10}$, or —$C^{\Phi}H(C(=O)R^9)(C(=O)R^{10}$;

$R^5$ is phenyl, benzyl, —$CH_2$-(4-hydroxy-phenyl), —$CH_2$-(indol-3-yl), —$CH_2$-(indol-4-yl), —$CH_2$-(napht-1-yl), —$CH_2$-(napht-2-yl), —$CH_2$-(aryl), —$CH_2$-(heteroaryl), napht-1-yl, or napht-2-yl;

$R^6$ is methyl, ethyl, propyl, isopropyl, n-butyl, i-butyl, t-butyl, (2S)-butyl, (2R)-butyl, $C_{5-6}$ alkyl, cyclopropyl, cyclopropylmethyl, cyclopentyl, cyclohexyl, cyclopentylmethyl, or cyclohexylmethyl;

$R^7$ is —O— or —$N(R^9)$—;

$R^8$, $R^9$ and $R^{10}$ are, independently in each instance, H, alkyl, cycloalkyl, aryl, heteroaryl, heterocyclic, or $(CH_2CH_2O)_n CH_3$;

m is 2, 3, 4 or 5;

n is an integer of from 1 to 20;

$C^{\alpha}$, $C^{\beta}$, $C^{\gamma}$, $C^{\epsilon}$ and $C^{\Phi}$ are carbon atoms, and the stereochemistries at $C^{\alpha}$, $C^{\beta}$, $C^{\gamma}$, $C^{\epsilon}$ and $C^{\Phi}$ are independently either R or S;

or pharmaceutically acceptable salt, hydrate, solvate, prodrug or solvate thereof.

In further embodiments, the compound may be selected from:

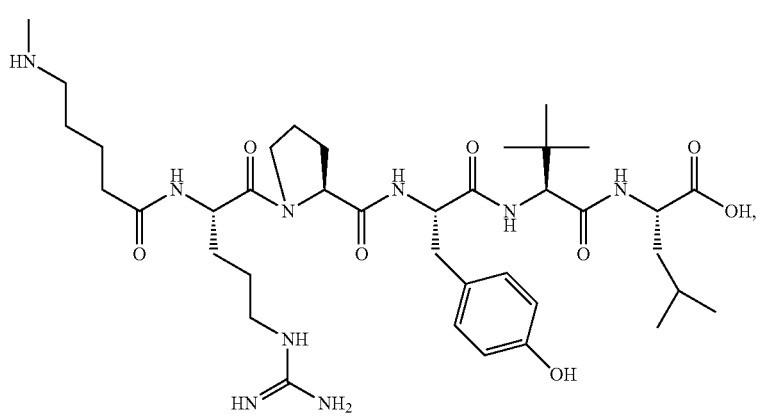

Figure 2:
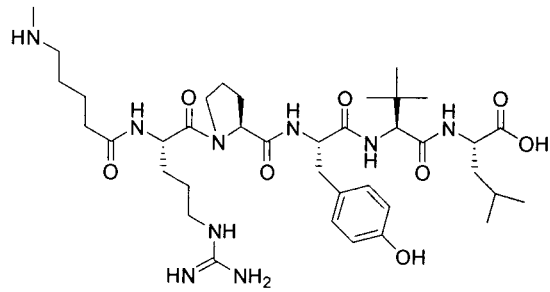
FIG. 2 illustrates the chemical structure of compounds HPI-234, HPI-244, HPI-262, HPI-263, HPI-264, HPI-363, and HPI-501.
Figure 2:
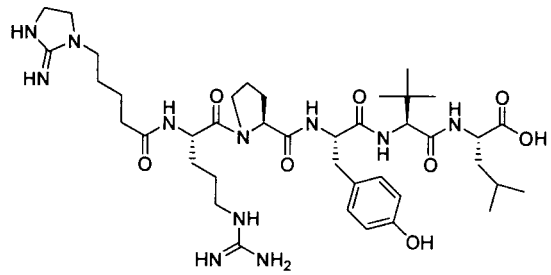
Figure 2:
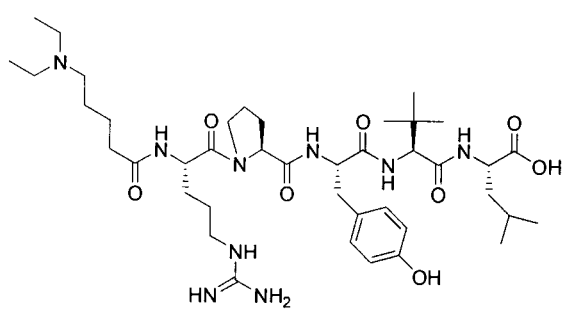
Figure 2:
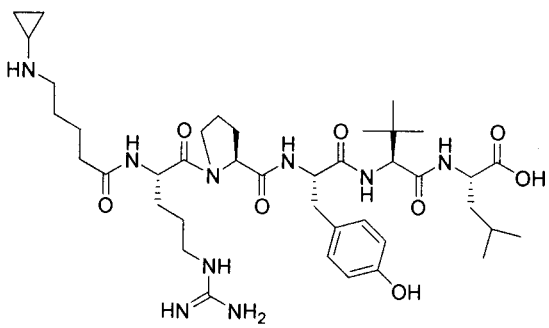
Figure 2:
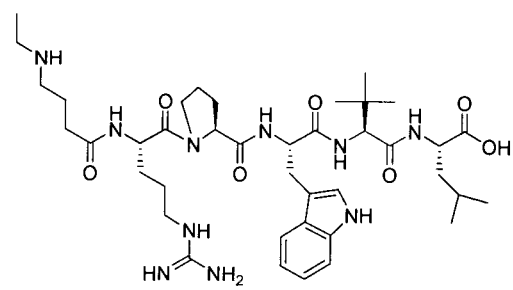
Figure 2:
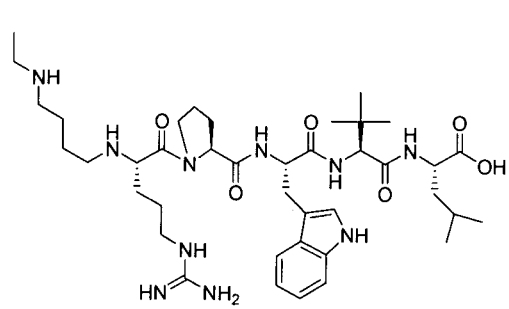

-continued
HPI-244
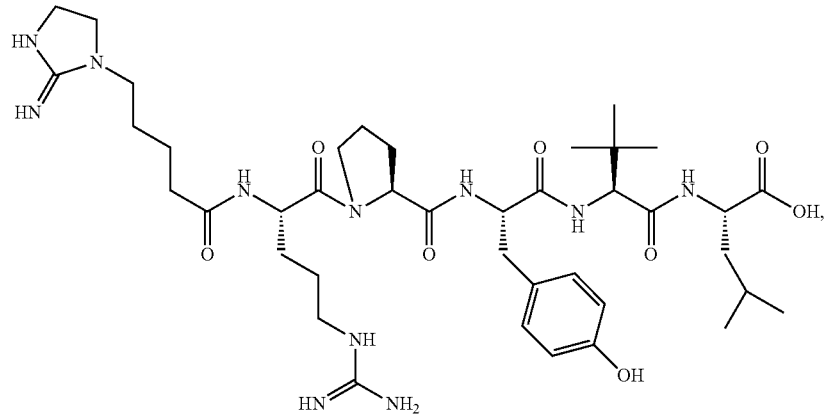
HPI-262
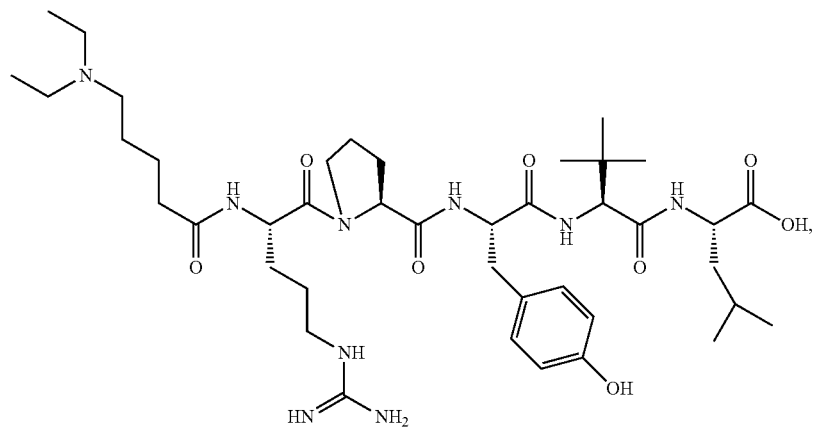
HPI-263
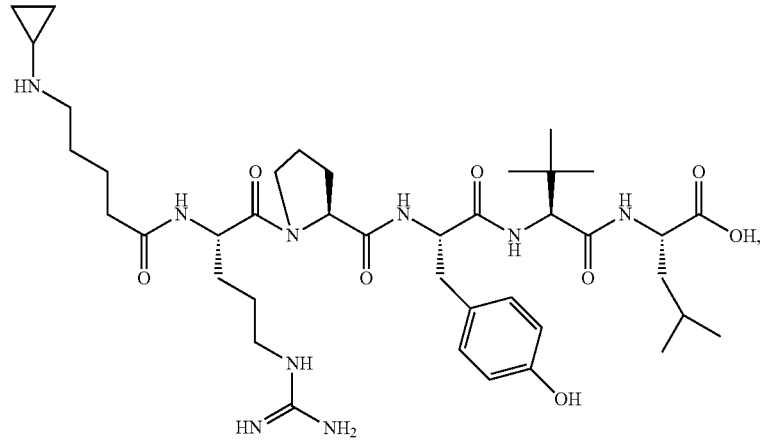
HPI-363                                    HPI-501
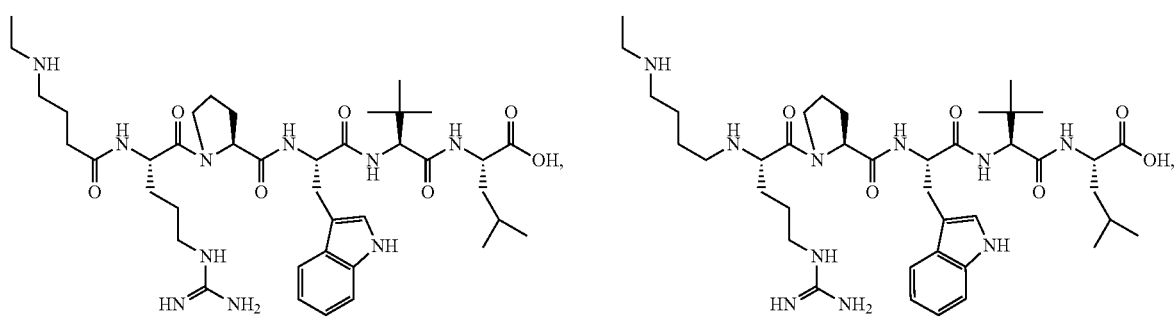

or a combination thereof. See FIG. 2. In some embodiments, the compound may be
HPI-363
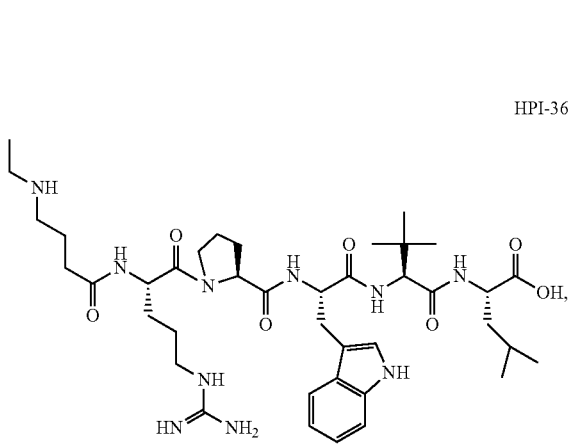
HPI-501
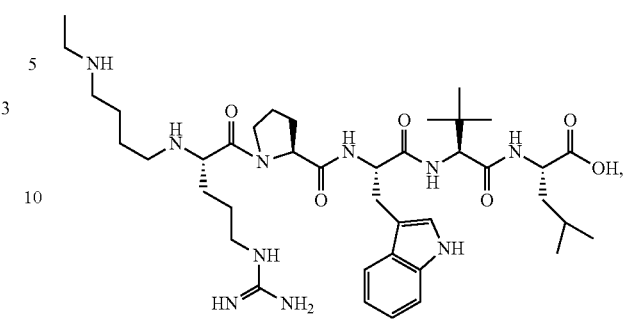
or a combination thereof.
Embodiments herein may be directed to a pharmaceutical composition comprising a compound having the structure of Formula I and a pharmaceutically acceptable excipient. In some embodiments, the compound may be selected from
HPI-234
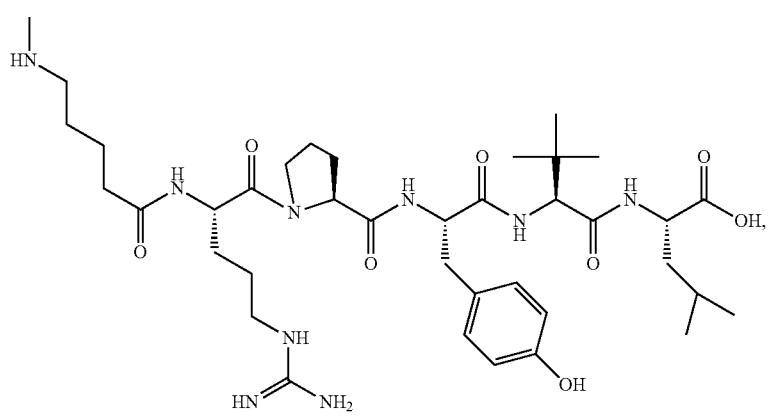
HPI-244
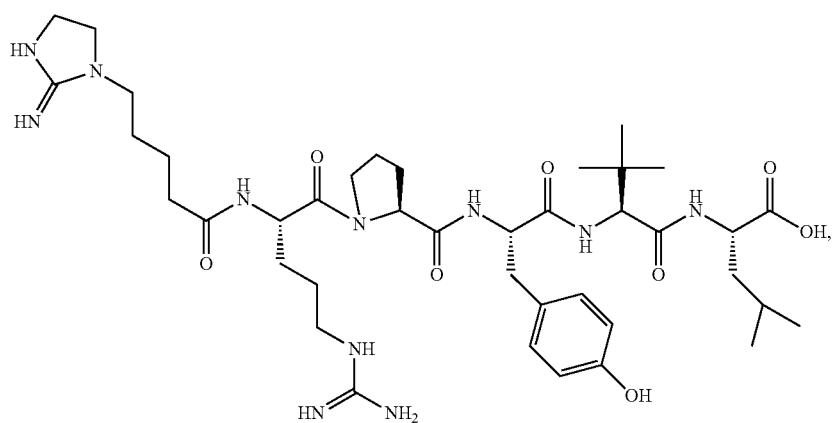

HPI-262
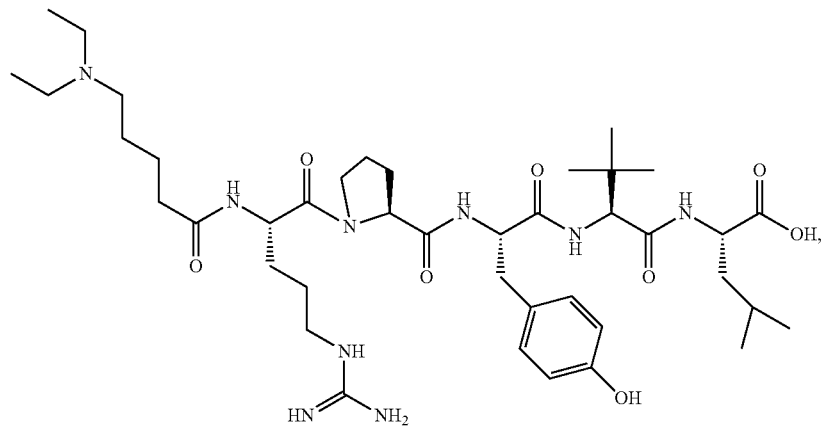
HPI-263
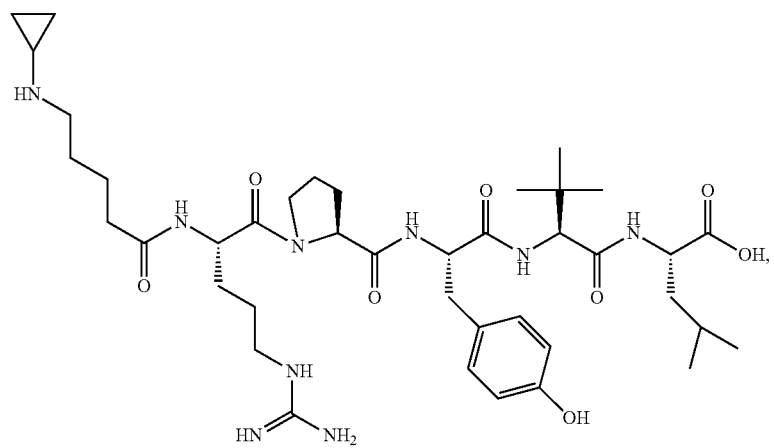
HPI-363
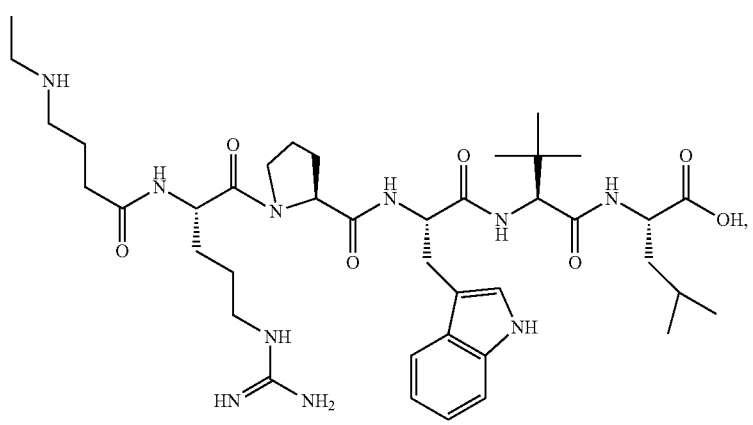

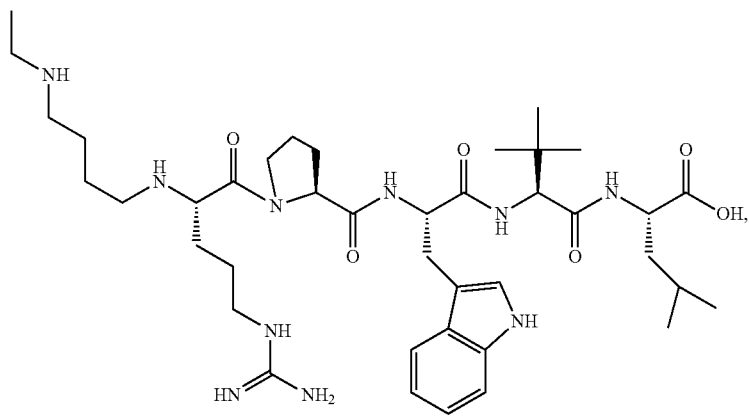

HPI-501 or a combination thereof. In some embodiments, the compound may be

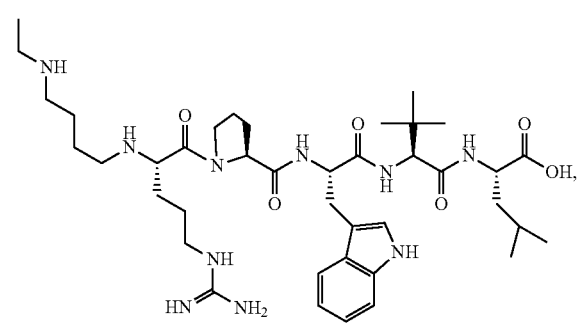

HPI-363

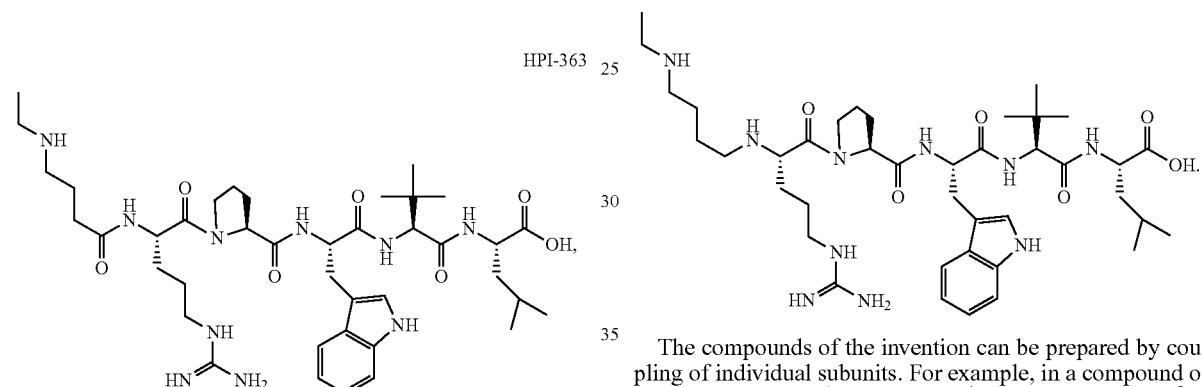

HPI-501 or a combination thereof. In some embodiments, the compound may be present in the composition in a therapeutically effective amount. In some embodiments, the compound may be present in the pharmaceutical composition in an amount from about 0.001 to about 99.9 wt %, from about 0.01 to 99 wt %, from about 0.01 to about 90 wt %, from about 0.01 to about 85 wt %, from about 0.1 to about 95 wt %, from about 0.1 to about 90 wt %, from about 0.1 to about 85 wt %, from about 1 to about 99.9 wt %, from about 1 to about 99 wt % from about 1 to about 95 wt %, from about 1 to about 90 wt %, from about 1 to about 85 wt %.

Embodiments described herein may be directed to a compound having the formula:

HPI-501

The compounds of the invention can be prepared by coupling of individual subunits. For example, in a compound of Formula I where $R^1$ is methyl, $R^4$ is —$(CH_2)_4NH_2$, $R^5$ is benzyl, $R^6$ is sec-butyl, $R^7$ is —O— and $R^8$ is H, the subunits could be construed as being acetic acid, lysine, proline, phenylalanine, isoleucine and leucine, as shown below. This example only exemplifies the possibility of envisioning the compound of Formula I as being composed of different subunits and should be not considering as introducing any limitation or preference in this disclosure.

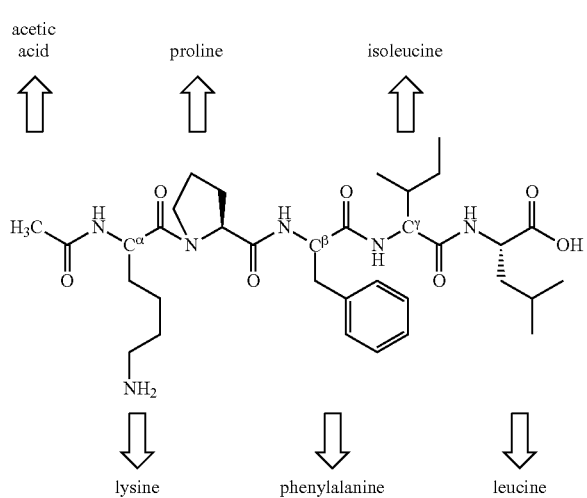

In embodiments, the compounds of Formula I are composed of subunits connected by amide bonds. Therefore, such compounds could be prepared by formation of amide bonds between the various subunits. Each subunit can be an amino acid, an acid or an amine.

In embodiments, the subunits may contain substituents on their side chains, and such substituents may include amino groups, carboxylate groups or arginino groups, for example. One skilled in the art would appreciate that such side chain groups may require protection with a protective group before creation of the amide group between the subunits. After the formation of the amide group or at any later stage in the synthesis, the protective group of the side chain group may then be removed. See, for example, the review of amine protecting groups provided in "Compendium of Organic Synthetic Methods", I&S Harrison, Wiley Interscience, New York, N.Y. (1971), the disclosure of which is incorporated herein by reference. For side chain amino groups, some of the preferred protective groups are Boc (tert-butoxy carbonyl) and Fmoc (fluorenylmethoxy carbonyl). These groups may be removed by treatment with acid, such as trifluoroacetic acid, and base, such as piperidine, respectively. The side chains of the subunits may also incorporate substituents that may be modified into other substituents at a later stage in the synthesis. For example, a nitro group in the side chain may be reduced to an amino group if so desired.

In embodiments, the subunits required for the synthesis of the compounds described herein may be purchased from commercial sources or prepared by standard synthetic methods known to those skilled in the art. Designing appropriate synthetic routes for each subunit is within the capabilities of those skilled in the art. Since the subunits will be covalently coupled to other subunits through amide bonds, it may be convenient to employ as starting materials conveniently protected subunits, which can be deprotected at a later stage of the synthesis. A protective subunit may be chosen which does not get cleaved under the coupling conditions but may be cleaved under conditions mild enough to avoid decomposition of the compound of the invention or any intermediate in its synthesis.

In embodiments, the subunits of the compounds described herein may be, partially or in totality, assembled by the Merrifield solid phase method, which is an established method for preparing peptides to those skilled in the art. See Merrifield, 1986, Science 232, 341, the disclosure of which is incorporated herein by reference. Alternatively, in other embodiments, the peptide minus one or more of the N-terminal units may be expressed recombinantly by known biological methods, and the final N-terminal residue or residues may be added by chemical methods or by enzymatic condensation with an aminopeptidase. See "Enzyme Structure and Mechanism", Alan Fersht, W.H.Freeman, New York, N.Y. (1985), the disclosure of which is incorporate herein by reference.

The Merrifield solid phase synthesis may be generically outlined as shown below. Starting with an appropriate anchor resin designed for amino group exposure, the carboxy terminus amino acid unit of the peptide having an amino protecting group such as an Fmoc group is anchored to the resin through a selectively cleavable carboxyl coupling link. The amino group of the anchored carboxy terminus unit is then deprotected, and the additional amino protected amino acid units are then sequentially coupled in proper sequence. Each coupling step will involve deprotection of the protected amino group of the anchored peptide chain, followed by peptide condensation between that unprotected amino group and the carboxyl group of the next amino acid unit. The condensation may be facilely obtained by carbodiimide coupling, by Schotten Bauman reaction or by activated acyl group condensation. These condensation reactions are described in "Advanced Organic Chemistry", 4$^{th}$ edition, J. March, Wiley Inter-Science, New York, N.Y. (1992). Protection of amine, carboxyl or any other side chains using appropriate protecting groups that differ from the protecting groups of the $\alpha$-amino group entering into the peptide condensation will enable selective peptide condensation of the sequential amino acid units. Selection of appropriate protection groups and conditions for solid phase peptide synthesis are described by Merrifield (1986, cited above).

As a non-limiting example of a solid-phase synthesis sequence that may be used to prepare the compounds of the invention, resin-bound N$\alpha$-Fmoc-leucine may be swelled in DMF (dimethylformamide) and then the Fmoc group can be cleaved with piperidine (20% in DMF). The piperidine solution may be removed with vacuum filtration and the resin-bound amino acid washed with DMF and methylene chloride. Amino acids (4 equivalents) may be activated in DMF using HOBt (N-hydroxy-benzotriazole, 4 equivalents), PyBOP (benzotriazol-1-yl-oxy-tripyrrolidinophosphonium hexafluorophosphate, 4 equivalents) and DIPEA (diisopropylethylamine, 10 equivalents) and added directly to the peptide reaction vessel. The amino acid couplings may be conducted for approximately 6 hours, the resin washed with DMF and methylene chloride and monitored for the presence of free amines using the Kaiser test (Kaiser et al., 1970, Anal. Biochem. 34: 595-8). Residues may be recoupled if necessary. The procedure may be repeated with subsequent amino acids to form the desired peptide. Acid-catalyzed deprotection may be performed with a trifluoroacetic acid (TFA) solution containing appropriate scavengers, and crude peptides may be precipitated in ice-cold ether.

In some embodiments, parts or the entirety of the peptide may also be produced by recombinant expression. This biological method involves reengineering a microbe to express parts or the entirety of the peptide. In embodiments, a DNA sequence encoding the sequence of parts or the entirety of the peptide may be inserted in proper reading form into a plasmid or other vector capable of causing microbial expression of the DNA. In some embodiments, the vector may also contain appropriate control, promoter and selection DNA segments. Upon insertion into a microbe such as *E. coli* or *B. subtilus*, the microbe mixture may be selected for appropriate transfection by treatment with the corresponding selection agent. In embodiments, the agent may be an antibiotic. In further embodiments, the vector may contain a sequence encoding the corresponding detoxifying enzyme for the antibiotic. Chloramphenacol and penicillin are two of such agents. Culturing the transfected microbe and harvesting the expressed peptide, as either secreted material of the culture medium or by lysing the microbe cells, will provide the crude peptide. The peptide may be purified by known techniques such as lyophilization, chromatography (such as reverse phase high pressure liquid chromatography) and the like. These recombinant techniques for peptide expression are fully set forth in "Cold Spring Harbor—Current Protocols in Molecular Biology", Wiley InterScience, Cold Spring Harbor (2003), the disclosure of which is incorporated herein by reference.

In some embodiments, the compounds described herein may have structural similarity to the natural peptide neurotensin and may display similar biological activity to this natural peptide. Neurotensin (NT) is a thirteen amino acid peptide that appears to have functions as a neurotransmitter and neuromodulator in the nervous system (and as a local hormone in the periphery). In the periphery, neurotensin is a paracrine and endocrine modulator of the digestive tract and acts as a growth factor on a variety of cells. The peptide has been implicated in the regulation of gastro-intestinal functions. Fat ingestion induces a dose-related increase in neurotensin plasma concentrations. Neurotensin has a number of physiological functions that include the stimulation of pancreatic exocrine secretion, inhibition of gastric secretion, and inhibition of gastroduodenal motility. Peripherally, NT acts as a hormone to induce hypotension and decrease gastric acid secretion. Structurally, NT is a linear tridecapeptide with the following sequence: pGlu-Leu-Tyr-Glu-Asn-Lys-Pro-Arg-Arg-Pro-Tyr-Ile-Leu-OH, where pGlu is the cyclic analogue of the natural L-glutamate amino acid. The C-terminal hexapeptide $Arg^8$-$Arg^9$-$Pro^{10}$-$Tyr^{11}$-$Ile^{12}$-$Leu^{13}$ [known as NT(8-13)] is equipotent at producing the physiological effects of NT in vitro and in vivo. This indicates that NT(8-13) is the active fragment.

$NT_1$ and $NT_2$ receptors are G-protein-coupled receptors (GPCRs), whereas $NT_3$ is a non GPCR. $NT_1$ receptor has been the receptor most strongly implicated in a number of effects such as food intake, modulation of body temperature, pain response, locomotor activity, memory, sensorimotor gating. Efforts have been directed to targeting $NT_1$ receptors as a strategy to develop novel treatments for several CNS disorders, most notably schizophrenia. Other efforts have been directed at developing NT agonists that can penetrate the blood-brain-barrier (BBB) after peripheral administration since natural NT is has an extremely short half-life as it is prone to rapid cleavage by different peptidases.

Dyslipidemia is characterized by abnormal lipid levels of one or more lipids (e.g. cholesterol and triglycerides), and/or apo-lipoproteins (e.g. apo-lipoproteins A, B, C and E), and/or lipoproteins (e.g. Low Density Lipoproteins (LDL), Very Low Density Lipoproteins (VLDL) and Intermediate Density Lipoproteins (IDL)), which may reflect one of several disorders in the metabolism of lipoproteins. Although treatment options exist, contemporary therapeutic agents for treating dyslipidemia possess variable efficacy and considerable adverse safety profiles that limit their full clinical utility. The pharmacokinetic and transport properties of NT(8-13) limit its practicality as a therapeutic agent. Accordingly, a therapeutic gap exists for a more efficacious and safer method to treat dyslipidemia, including among others, with suitable novel pharmaceutical compositions of neurotensin analogs thereof, delivery methods, and the like.

Cholesterol is mostly carried in Low Density Lipoproteins (LDL). LDL-cholesterol is commonly known as the "bad" cholesterol because it has been shown that elevations in LDL-cholesterol correlate closely to the risk of coronary heart disease. A smaller component of cholesterol is carried in the High Density Lipoproteins (HDL) and is commonly known as the "good" cholesterol. The primary function of HDL is to accept cholesterol deposited in the arterial wall and to transport it back to the liver for disposal through the intestine. Thus, it is desirable to lower elevated levels of LDL cholesterol and to increase levels of HDL cholesterol. Increased levels of HDL may be associated with a lower risk for coronary heart disease (CHD).

Triglycerides (TG) are not "cholesterol" but are another form of lipid in the body. Non-lipid risk factors of obesity, hypertension, diabetes, and cigarette smoking are also interrelated with triglycerides as are several emerging risk factors (insulin resistance, glucose intolerance, and prothrombotic state). Thus, people with elevated triglycerides may be at an increased risk for cardiovascular disease (CVD). In addition, elevated triglycerides are associated with other disorders, most notably pancreatitis.

Though not used commonly in primary care for the usual diagnosis and treatment of dyslipidemia, the Fredrickson Classification, performed using lipoprotein plasmaphoresis, has been the traditional and remains the most rigorous method for classifying dyslipidemia. The Fredrickson Classification includes 6 phenotypes (i.e., I, IIa, IIb, III, IV and V) with the most common being the isolated hypercholesterolemia (or Type IIa) which is usually accompanied by elevated concentrations of total and LDL cholesterol. The initial treatment for hypercholesterolemia is often to modify the diet to one low in fat and cholesterol, coupled with appropriate physical exercise, followed by drug therapy when LDL-lowering goals are not met by diet and exercise alone.

Another common form of dyslipidemia is the mixed or combined hyperlipidemia or Type III) and III of the Fredrickson Classification. This dyslipidemia is often prevalent in patients with Type II diabetes, obesity and metabolic syndrome. In this form of dyslipidemia there are modest elevations of LDL-cholesterol, accompanied by more pronounced elevations of small dense LDL-cholesterol particles, VLDL and/or IDL (i.e., triglyceride rich lipoproteins), and total triglycerides. In addition, concentrations of HDL are often low in these patients.

Coronary Heart Disease (CHD), the largest component of death related to CVD, is caused by atherosclerosis, i.e., hardening of an artery due to an atheromatous plaque. The formation of an atheromatous plaque, known as atherogenesis, is a complex process involving both cellular and acellular elements of cholesterol, cholesterol esters, and phospholipids. According to the Third Report of the National Cholesterol Education Program—Adult Treatment Panel (NCEP-ATP) III, atherogenic dyslipidemia is defined as the triad of elevated triglycerides, low HDL-C, and small LDL-C particles. This triad is most commonly found in individuals with an atherogenic phenotype and/or Type II Diabetes Mellitus (DM), and treatment involves lowering triglycerides and increasing HDL-C by diet modification, increased exercise, and pharmacologic therapy with one or more of the following: HMG-CoA reductase inhibitors (statins), fibrates, nicotinic acid (i.e. Niacin), cholesterol adsorption inhibitors, bile acid binding resins, and omega-3-fatty acids. However, each has its own drawbacks and limitations in terms of efficacy, side-effects, and qualifying patient population.

Treating abnormal lipid concentrations to prevent atherosclerotic events focuses strongly on LDL-cholesterol reduction. The treatment goal is set for, depending on the absolute risk, an LDL-cholesterol of <100 mg/dL (optional<70 mg/dL) in patients with high risk (i.e., >20% event rate/10 years) or an LDL-cholesterol<130 mg/dL (intermediate risk) or an LDL-cholesterol<160 mg/dL (low risk). The primary drug treatment used to achieve these goals is usually a statin. Several approaches exist for patients with elevated LDL-cholesterol even though taking a statin. These include increasing the dose of the statin, switching to a more potent statin, combining the statin with a cholesterol absorption inhibitor (ezetimibe) or combining a statin with a bile acid binding compound (i.e., colesevelam). For patients on a statin with abnormal triglyceride and/or HDL-cholesterol concentrations combination therapy of a statin with niacin may be a treatment option. The combination of statins with either a fibrate or omega-3 fatty acids may be alternatives. Primary fibrate or niacin therapy or treatment with omega-3 may be considered for patients with isolated hypertriglyceridemia fatty acids.

Embodiments describe a method for treating a lipid disorder including, but not limited to, hyperlipidemia, hypercholesterolemia, and dyslipidemia, by modulation of one or more neurotensin receptors using one or more neurotensin analogs. Lipid disorders are considered as the abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as Low Density Lipoproteins (LDL), Very Low Density Lipoproteins (VLDL) and Intermediate Density Lipoproteins (IDL)). Without wishing to be bound by theory, it is believed that the treatment of diseases or conditions associated with dyslipidemia may be achieved through the modulation of the neurotensin receptors. In embodiments, a composition capable of binding to a neurotensin receptor may be exposed to at least one cell, a tissue, a vessel, or an organ, of a subject. The compounds of embodiments herein may be formulated to enable exposure or delivery to a subject with various drug delivery methods and devices. The treatment may be packaged within a kit and the kit may optionally include instructions, accessories or a combination thereof. In some embodiments, the composition may be administered in conjunction with statin, fibrate, niacin, omega-3 fatty acid, or a combination thereof.

In some embodiments, a method of normalizing abnormal lipid concentrations in a subject comprises administering a compound including the structure of Formula I to a subject in need thereof. See FIG. 1. In some embodiments, the abnormal lipid concentration may be selected from total lipid concentration, total cholesterol concentration, total apolipoprotein concentration, total lipoprotein concentration, LDL concentration, VLDL concentration, IDL concentration, HDL concentration, HDL-cholesterol concentration, LDL-cholesterol concentration, triglycerides, or a combination thereof. In some embodiments, a method of reducing levels of lipids comprises administering a compound including the structure of Formula I to a subject in need thereof. In some embodiments, the level of lipids may be lowered in subjects with abnormal lipid levels. In some embodiments, the level of lipids may be lowered in subjects with abnormally high lipid levels. In some embodiments, the level of lipids may be lowered in subjects with abnormally low lipid levels. In some embodiments, the level of lipids may be reduced in subjects with normal lipid levels. In some embodiments, the level of lipids comprises the level of cholesterol, triglycerides or a combination thereof. In some embodiments, a method of lowering lipid concentrations comprises administering a compound including the structure of Formula I to a subject in need thereof. In some embodiments, the lipid concentration may be selected from total lipid concentration, total cholesterol concentration, total apolipoprotein concentration, total lipoprotein concentration, LDL concentration, VLDL concentration, IDL concentration, LDL-cholesterol concentration, triglycerides, or a combination thereof. In some embodiments, a method of increasing the ratio of HDL concentration to LDL concentration comprises administering a compound including the structure of Formula I to a subject in need thereof. In some embodiments, the HDL concentration is the concentration of HDL-cholesterol. In some embodiments, the LDL concentration is the concentration of LDL-cholesterol. In some embodiments, a method of increasing HDL concentration comprises administering a compound including the structure of Formula I to a subject in need thereof. In some embodiments, the HDL concentration is the concentration of HDL-cholesterol. In some embodiments, the total lipid concentration comprises the sum of cholesterol and triglyceride concentrations. In some embodiments, the total cholesterol concentration comprises the sum of HDL-cholesterol and LDL-cholesterol concentrations. In some embodiments, the total apolipoprotein concentration comprises the sum of the concentrations of apolipoproteins A, B, C, and E. In some embodiments, the total lipoprotein concentration comprises the sum of the concentrations of HDL, LDL, VLDL and IDL.

In some embodiments, a method of treating a lipid disorder comprises administering a compound including the structure of Formula I to a subject in need thereof. See FIG. 1. In some embodiments, the compound may be selected from HPI-234, HPI-244, HPI-262, HPI-263, HPI-264, HPI-363, HPI-501 or a combination thereof. See FIG. 2. In some embodiments, the lipid disorder may be one or more of the following diseases or conditions: hyperlipidemia, dyslipidemia, hypercholesterolemia, hypertriglyceridemia, hyperglycemia, and obesity. In some embodiments, the compound may be used to treat non-insulin dependent diabetes mellitus (NIDDM) and/or conditions that are often associated with NIDDM, but which may be present in non-diabetic patients as well, including hyperlipidemia, dyslipidemia, hypercholesterolemia, hypertrigyceridemia, and obesity. In some embodiments, the compound may be used to treat atherosclerosis and hyperinsulinemia. In some embodiments, the compound may be used to delay or reduce the risk of sequelae of NIDDM, for example, by ameliorating the conditions that contribute to the development of these diseases. In some embodiments, the compound may be used to reduce cardiovascular events that occur in human patients having metabolic syndrome, such as, for example, coronary heart disease, by ameliorating some of the risk factors that are associated with metabolic syndrome.

Some embodiments may be directed to a method of treating dyslipidemia comprising administering a compound including the structure of Formula I, as shown in FIG. 1, to a subject in need thereof. In some embodiments, the compound may be selected from

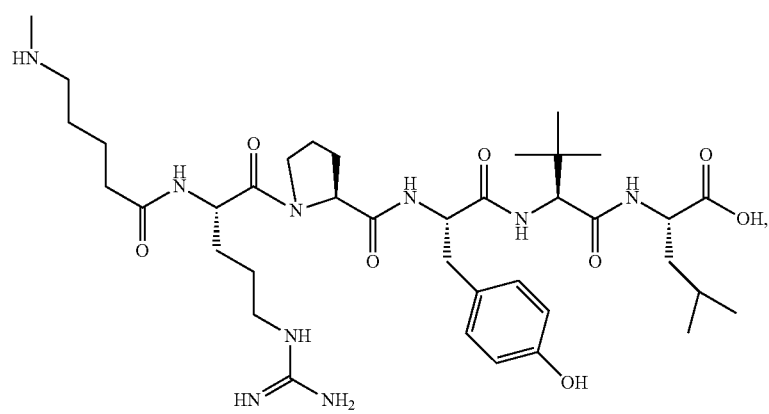

HPI-234

HPI-244
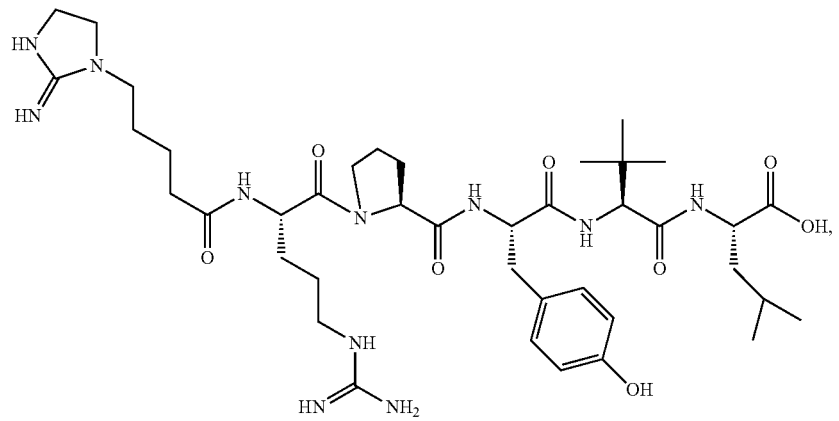
HPI-262
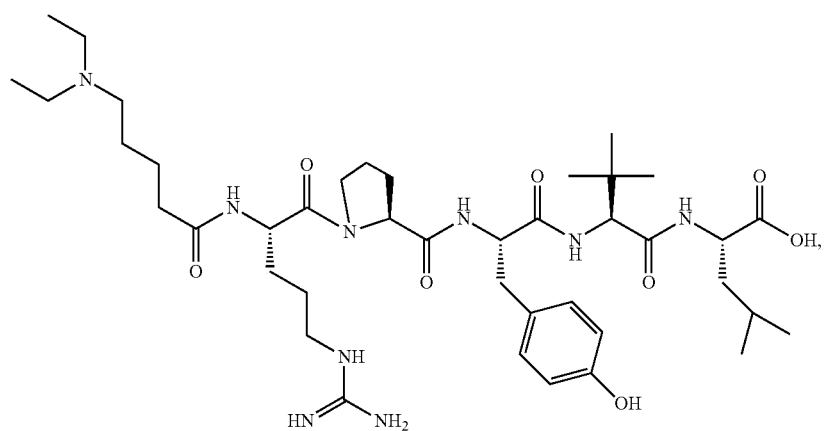
HPI-263
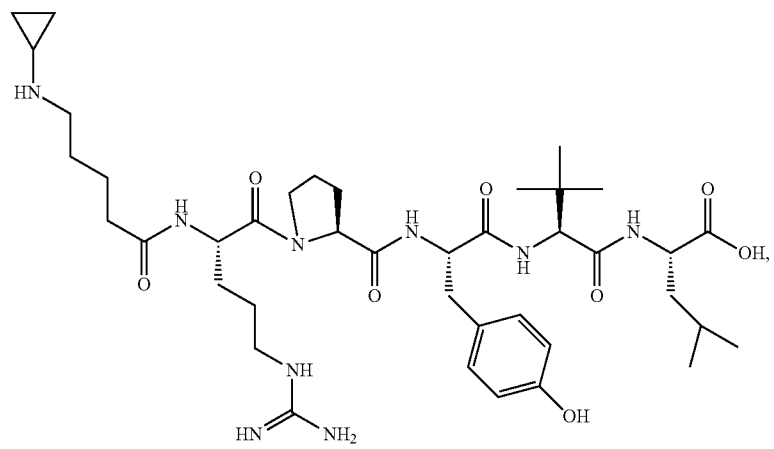

HPI-363

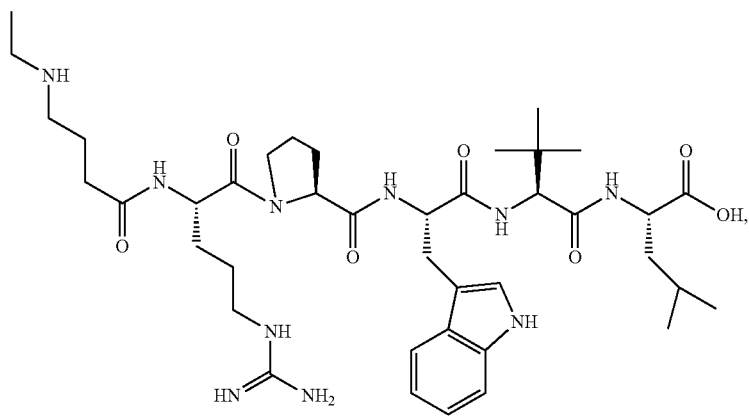

HPI-501

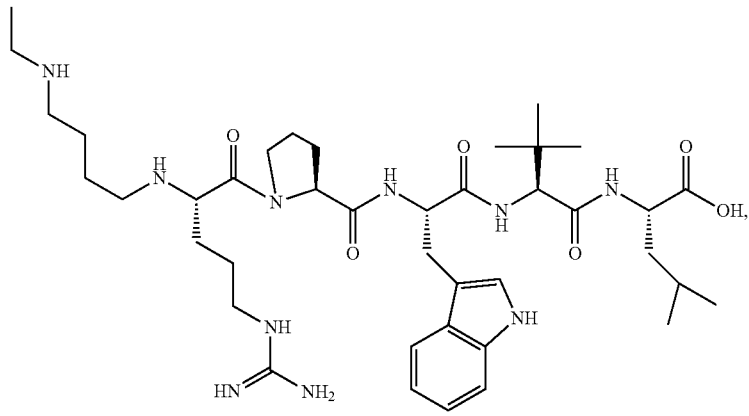

or a combination thereof. In one embodiment, a method is provided for the modulation of a signaling pathway associated with a neurotensin receptor comprising administering a compound including the structure of Formula I to a subject in need thereof. In some embodiments, the signaling pathway may be intracellular, extracellular or a combination thereof. In some embodiments, the neurotensin receptor may be selected from $NT_1$, $NT_2$, $NT_3$, or a combination thereof. In some embodiments, administering to a subject comprises exposing the subject to the compound. In further embodiments, the subject is exposed to the compound in an effective amount. In some embodiments, the exposure step may be prior to, coincident with, or subsequent to an occurrence of dyslipidemia.

In some embodiments, the compounds of embodiments herein may be used to treat conditions associated with dyslipidemia. In some embodiments, a method of treating conditions associated with dyslipidemia comprises administering a compound having the structure of Formula I to a subject in need thereof. In embodiments, the conditions associated with dyslipidemia comprises atherosclerosis, pancreatitis, coronary heart disease, stroke, cardiac arrest, or the like.

Some embodiments provide for a method of treating lipid disorders in cells possessing a neurotensin receptor including, but not limited to, epithelial cells, epithelial-like cells, endothelial cells, endothelial-like cells, non-epithelial cells, non-endothelial cells, neuronal cells, intestinal cells and the like. In some embodiments, the neurotensin receptor may be selected from $NT_1$, $NT_2$, $NT_3$ or combinations thereof. In certain aspects, the cells may include, but are not limited to, stem cells, autogenic, allogenic, xenogenic or genetically-modified variants of any one of the foregoing cell types. According to some embodiments, the cells may include, without limitation, vascular endothelial cells, pancreatic cells, hepatic cells, brain cells, immune cells, among others. Embodiments herein also include a method of treating the tissues and organs containing such cells.

In some embodiments, the compounds used in the methods herein may be administered as a pharmaceutical composition, comprising the compound and a pharmaceutically acceptable carrier. The compound may be present in a pharmaceutical composition in an amount from 0.001 to 99.9 wt %, more preferably from about 0.01 to 99 wt %, and even more preferably from 0.1 to 95 wt %.

A truncated COOH-terminal fragment NT (8-13) has been found to be slightly more stable while maintaining neurotensin receptor affinity. However, even the half-life of NT (8-13) may be too brief. One approach that has led to the development of several distinct brain penetrating NT analogs has been chemical modification of the c-terminal hexapeptide of NT, NT (8-13), the smallest fragment to retain full bioactivity of the parent neuropeptide. PD149163, (Lys-(psiCH2NH)-Lys-Pro-Trp-Ter-Leu-Leu-OEt) is one example of a compound synthesized using this approach and receptor binding studies show it has affinity for the $NT_1$ receptor but no detectable affinity for the $NT_2$ receptor. Peripheral administration of PD149163 has been shown to produce robust positive effects in animal tests of antipsychosis, cognitive enhancement, anxiety, and decreased food intake as a potential treatment candidate for obesity (Feifel et. al, Neuropharmacology 58:195-198 (2010)). On the other hand, chemical modification of the NT (8-13) may be made at the N-terminus and substitutions of specific amino acids of the NT (8-13) sequence using non natural amino acids as well desamino acids (see US Applications 20100130432, 20080234202, 20080139481).

Embodiments herein describe compounds having N-terminus or C-terminus modifications of NT. In some embodiments, the compound is a truncated COOH-terminal fragment of NT(8-13). Such NT-derived analogs may be used for the treatment of several diseases and conditions including, without limitation, obesity, hyperlipidemia, hypercholesterolemia, dyslipidemia, and other lipid disorders. In some embodiments, the treatment of dyslipidemia may delay the onset of or reduce the risk of conditions and sequelae that are associated with abnormal plasma lipid concentrations, including, without limitation, atherosclerosis and non-insulin dependent diabetes.

NT induces hypothermia when directly administered into the CNS. As a result, induced hypothermia may be used to determine the ability of NT(8-13) analog peptides to cross the blood-brain barrier after peripheral administration and indirectly to determine their in vivo CNS activity. Without wishing to be bound by theory, it is believed that the hypothermic effect of NT can be attributed to its actions at NTRi. A significant hypothermic effect would demonstrate that the peptide showed marked improvements in blood stability and membrane crossing. In embodiments, IP injection is the standard route of administration to determine the extent of BBB crossing of neurotensin analogues. In other embodiments, IV administration results in a dose that is completely available to the systemic circulation.

In some embodiments, the compounds described herein may have the unexpected ability to ameliorate, avoid or treat perioperative shivering or temperature spiking in a mammal. These neurological activities may be traced to the specific interactions of the compounds of the invention within the central nervous system (CNS). In some embodiments, the compounds may be able to penetrate the CNS to engage in these specific interactions and display biological activities.

Embodiments include a method of exposing or applying a compound of embodiments herein to, onto, into, within, or throughout a cell, tissue, or organ of a subject. In certain embodiments the composition may be applied with a fixed concentration or mixture ratio. In certain embodiments, the composition may be applied with varying concentrations or mixture ratio over time. In certain embodiments, application may be performed intermittently, periodically, or continuously, over a period to time; seconds, minutes, hours, days, 5 days, 10 days, weeks, months, or any length of time in between. In other embodiments, application may be performed simultaneously with other therapeutic agents known in the art, in similar said manners.

In embodiments, the compound may be administered by any method designed to allow compounds to have a physiological effect. In other embodiments, the compound may be administered in the conventional manner by any route in which it is active. Compounds of embodiments herein may be used for prophylactic or therapeutic treatment or a combination thereof. The pharmaceutical compositions may be administered in a variety of unit dosage forms depending upon the method of administration. In some embodiments, administration may occur enterally or parenterally; for example orally, rectally, intracisternally, intravaginally, intraperitoneally or locally. In preferred embodiments, administration may be parenteral or local administration.

In some embodiments, the composition, or analogs thereof, may be formulated and incorporated into devices for various routes of delivery, including but not limited to transdermal, mucosal, jet injection, topical, intravenous, intramuscular, pulmonary, inhalation, nasal, aerosol, buccal, oral, the like, and combinations thereof A formulation containing one or more said compound or analogs thereof, may be incorporated into liquid nebulizers, aerosol-based metered dose inhalers (MDI's), dry powder dispersion devices, pulmonary delivery devices, including manually activated, gas propelled, sonic-driven, or the like, used to expose the formulation to a subject's cell, tissue, and organs. The formulation may contain other agents, or in a carrier, to facilitate but not limited to, its delivery, in specific or varying concentrations or ratio, or volume, or weight that specifies the properties of the composition including pH, hydrophobicity, hydrophilicity, ionic strength, stability, buffer capacity, and the like.

Administration may be systemic, topical, or oral. For example, administration may be, but is not limited to, parenteral, subcutaneous, intravenous, intramuscular, intraperitoneal, transdermal, oral, buccal, or ocular routes, intravaginally, by inhalation, by depot injections, or by implants. Further, modes of administration for the compounds include, but are not limited to, sublingual, injectable (including, without limitation, short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

Specific modes of administration may depend on the indication. The selection of the specific route of administration and the dose regimen may be adjusted or titrated by the clinician according to methods known to the clinician in order to obtain the optimal clinical response. In some embodiments, the composition is administered in a therapeutically effective amount. In embodiments, the dosage to be administered may depend on the characteristics of the subject being treated, e.g., the particular animal treated, age, weight, health, types of concurrent treatment, if any, and frequency of treatments, and can be easily determined by one of skill in the art (e.g., by the clinician).

In some embodiments, single or multiple administrations of the compositions may be administered depending on the dosage and frequency as required and tolerated by the subject. In some embodiments, the compounds may be administered in separate compositions. For example, if three different compounds of the invention are to be administered, the three different compounds may be delivered in three separate compositions. In other embodiments, each compound may be delivered at the same time, or the compounds can be delivered consecutively with respect to one another. In some embodiments, a mixture of different compounds of embodiments herein may be administered in a single composition, or in multiple compositions comprising one or more compounds.

The regimen of administration can affect what constitutes an effective amount. The therapeutic formulations can be administered to the mammal either prior to or after the onset of lipid disorders in the mammal. Further, several divided dosages, as well as staggered dosages, can be administered daily or sequentially, or the dose can be continuously infused, or can be a bolus injection. Further, the dosages of the therapeutic formulations can be proportionally increased or decreased as indicated by the exigencies of the therapeutic or prophylactic situation.

In some embodiments, the compounds may be formulated in unit dosage form. As used herein, the term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. In embodiments, the unit dosage form may be for a single daily dose or one of multiple daily doses (e.g., about 1 to 4 or more times per day). In embodiments where multiple daily doses are used, the unit dosage form may be the same or different for each dose. In embodiments, the specifications for the unit dosage forms of the invention may be dictated by and may directly dependent on: (a) the unique characteristics of the therapeutic compound and the particular therapeutic effect to be achieved, and (b) the limitations inherent in the art of compounding/formulating such a therapeutic compound for the treatment of dyslipidemia.

In some embodiments, the composition may be administered in other dosage forms including, without limitation, dosage forms described in U.S. Pat. Nos. 6,340,475; 6,488,962; 6,451,808; 5,972,389; 5,582,837; 5,007,790 or U.S. Patent Publication Nos. 20030147952; 20030104062; 20030104053, 20030044466, 20030039688, and 20020051820. In some embodiments, the dosage forms may include, without limitation, dosage forms described in PCT Application Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

In some embodiments, a suitable dose of a compound of embodiments herein may be in the range of from about 1 mg to about 5,000 mg per day, or from about 10 mg to about 2,000 mg per day. The dose may be administered in a single dosage or in multiple dosages, for example, from 1 to 4 or more times per day. In embodiments where multiple dosages are used, the amount of each dosage may be the same or different. For example, in some embodiments, a dose of 1 mg per day can be administered as two 0.5 mg doses, with about a 12 hour interval between doses.

In some embodiments, a dose of a compound of embodiments herein may be between about 1 mg and about 2,000 mg. In some embodiments, a dose of a compound of the invention used in compositions described herein may be from about 2 mg to about 1,000 mg. In some embodiments, a dose of a compound of the invention used in compositions described herein may be from about 1 mg to about 1000 mg, about 1 mg to about 500 mg, about 1 mg to about 250 mg, about 1 mg to about 200 mg, about 1 mg to about 100 mg, about 10 mg to about 1000 mg, about 10 mg to about 500 mg, about 10 mg to about 250 mg, about 10 mg to about 200 mg, about 10 mg to about 100 mg, about 50 mg to about 1000 mg, about 50 mg to about 500 mg, about 50 mg to about 250 mg, about 50 mg to about 200 mg, about 50 mg to about 100 mg, about 100 mg to about 1000 mg, about 100 mg to about 500 mg, about 100 mg to about 250 mg, about 100 mg to about 200 mg, about 200 mg to about 1000 mg, about 200 mg to about 500 mg, about 200 mg to about 250 mg, about 250 mg to about 500 mg, about 500 mg to about 1000 mg, about 4 mg to about 500 mg, about 8 mg to about 250 mg, about 16 mg and about 125 mg, about 30 mg to about 60 mg, or any combination thereof.

In some embodiments, the compound may be administered every day, every other day, every 2 days, every 3 days, every 4 days, every 5 days, and so forth. As an example, in an embodiment where the compound is in administered every other day at a dose of 5 mg/day, a 5 mg per day dose may be initiated on Monday with a first subsequent 5 mg per day dose administered on Wednesday, a second subsequent 5 mg per day dose administered on Friday, etc.

The composition may be administered either alone or in combination with other therapeutic agents. In some embodiments, the compounds described in embodiments herein may be administered in combination with other therapies commonly used for the treatment and control of hyperlipidemia, hypercholesterolemia, dyslipidemia, and other lipid disorders, as well as delaying the onset of or reducing the risk of conditions and sequelae that are associated with these diseases, including atherosclerosis and non-insulin dependent diabetes. In some embodiments, the compounds may be administered in combination with other active ingredients, such as, for example, adjuvants, protease inhibitors, or other compatible drugs or compounds where such combination is seen to be desirable or advantageous in achieving the desired effects of the methods described herein. In some embodiments, the compound may be administered in combination with drugs known to treat, prevent, or reduce dyslipidemia. In some embodiments, the other active ingredients may include statin, fibrate, omega-3 fatty acid, nicotinic acid, or a combination thereof.

In certain embodiments, the combination of compounds described herein may result in synergistic increase in effectiveness for treating lipid disorders, relative to effectiveness following administration of each compound when used alone, or such an increase can be additive. In some embodiments, compositions described herein include lower dosages of each compound in a composition, thereby avoiding adverse interactions between compounds and/or harmful side effects. In some embodiments, compounds given in combination may provide for greater efficacy in subjects who are either unresponsive or minimally responsive to each compound when used alone.

In some embodiments, a mixture of two or more compounds of embodiments herein may be administered in equimolar concentrations to a subject in need of such treatment. In another embodiment, two or more compounds may be administered in concentrations that are not equimolar. In other embodiments, two or more compounds may be administered as equal amounts, by weight, per kilogram of body weight. For example, the compounds of the invention may be administered in equal amounts, based on the weight of the subject. In some embodiments, the compounds of the invention may be administered in unequal amounts. In some embodiments, the amount of each compound of the invention to be administered is based on its biological activity.

In some embodiments, pharmaceutical compositions that are useful in the methods used in the practice of the invention may be prepared in formulations suitable for oral, rectal, intracisternal, intravaginal, intraperitoneal or local, or another route of administration. Other contemplated formulations include projected nanoparticles, liposomal preparations, resealed erythrocytes containing the active ingredient, and immunologically-based formulations.

Pharmaceutical formulations containing the compounds of the present invention and a suitable carrier may be solid dosage forms which include, but are not limited to, tablets, capsules, cachets, pellets, pills, powders and granules; topical dosage forms which include, but are not limited to, solutions, powders, drops, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer of the present invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, Modern Pharmaceutics, Banker & Rhodes, Marcel Dekker, Inc. (1979); and *Goodman & Gilman's The Pharmaceutical Basis of Therapeutics*, 6th Edition, MacMillan Publishing Co., New York (1980) can be consulted. In some embodiments, a method of treating dyslipidemia comprises administering the composition of embodiments herein in a physically applicable or implantable predetermined solid form of material containing the composition. In embodiments, the compositions may be preferably combined with a solid carrier that itself is bio-acceptable and suitably shaped for its use.

In some embodiments, the composition may be administered by parenteral administration. As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques. Particularly preferred parenteral administration methods include intravascular administration (e.g., intravenous bolus injection, intravenous infusion, intra-arterial bolus injection, intra-arterial infusion and catheter instillation into the vasculature), peri- and intratarget tissue injection, subcutaneous injection or deposition including subcutaneous infusion (such as by osmotic pumps), intramuscular injection, intraperitoneal injection, and direct application to the target area, for example by a catheter or other placement device.

In embodiments, formulations of a pharmaceutical composition suitable for parenteral administration comprise the active compound and a pharmaceutically acceptable carrier. In some embodiments, the carrier is an aqueous carrier. Examples of such carriers include sterile water or sterile isotonic saline. In some embodiments, such formulations may be prepared in a form suitable for bolus administration or for continuous administration. In some embodiments, injectable formulations may be prepared in unit dosage form. Such unit dosage forms may include, for example, ampules or multi dose containers containing a preservative.

In some embodiments, formulations for parenteral administration may include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In some embodiments of a formulation for parenteral administration, the compound may provided in dry (e.g. powder or granular) form for reconstitution with a suitable vehicle (e.g. sterile pyrogen free water) prior to parenteral administration of the reconstituted composition.

In certain embodiments, the compositions for parenteral administration may be prepared in the form of a sterile injectable aqueous or oily suspension or solution. In some embodiments, this suspension or solution may be formulated according to the known art, and may comprise, in addition to the active ingredient, additional ingredients such as the dispersing agents, wetting agents, or suspending agents described herein. Such sterile injectable formulations may be prepared using a non toxic parenterally acceptable diluent or solvent, such as water or 1,3-butanediol, for example. Other acceptable diluents and solvents may include, but are not limited to, Ringer's solution, isotonic sodium chloride solution, and fixed oils such as synthetic mono- or diglycerides. Other usual parentally-administrable formulations may include those that comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

In embodiments for parenteral administration, a variety of aqueous carriers may be used, e.g., buffered saline and the like. In embodiments, these suspensions may be sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The amount of the compound can vary widely, and will be selected primarily based on fluid volumes, viscosities, body weight and the like in accordance with the particular mode of administration selected and the subject's needs.

In embodiments, the composition may be administered by continuous infusion subcutaneously over a period of about 15 minutes to about 24 hours. The compositions may take such forms as suspensions, solutions or emulsions in oily or aqueous vehicles, and may contain formulatory agents such as suspending, stabilizing and/or dispersing agents.

In some embodiments, the pharmaceutical composition for intravenous administration may be in a dose of from about 1 to about 3,000 mg per subject per day. Dosages from about 1 to about 1,000 mg per subject per day may be used, particularly when the drug is administered to a secluded site and not into the blood stream, such as into a body cavity or into a lumen of an organ. Methods for preparing parenterally administrable compositions will be known or apparent to those skilled in the art and are described in more detail in such publications as Remington's Pharmaceutical Science, 15th ed., 1980, Mack Publishing Company, Easton (PA).

In an embodiment, the composition may be in the form of a solid formulated for oral delivery. In certain embodiments, the composition may be the form of a powder that can be made soluble or reconstituted with a buffer solution or a carrier. In certain embodiments, the composition may be in the form of a capsule formulated for oral delivery. In certain embodiments, the composition may be in form of a dry powder formulated for pulmonary delivery. In certain embodiments, the composition may be in form of an aerosol liquid droplet formulated for pulmonary delivery. In certain embodiments, the composition may be in the form of an emulsion formulated for topical exposure to the subject. In an embodiment, the compositions may be incorporated in a topical vehicle in the form of a patch, a gel, a hydrogel, a wound dressing, a gauze, a sponge, a cloth, an absorbent pad, a cream, a lotion, a stick, an ointment, a gel, a spray, a foam, an aerosol, a liquid drop, or the like. In another preferred embodiment, the said compositions and various combinations are delivered via a liposome or the like. In some embodiments, the compositions can be statically bound to the surface of a liposome, covalently attached to the surface of a liposome, or encapsulated within a liposome. In some embodiments, the compositions may be statically bound to the surface of a particle, covalently attached to the surface of a particle, or encapsulated within a particle or a shell. In some embodiments, the formulations and delivery vehicles may be configured for specific therapeutic transport characteristics including but not limited to pulsatile, rapid, continuous, sustained-release, controlled-release, and combinations thereof. In some embodiments, the compositions may contain other agents that enable sufficient, efficient, and effective delivery for the treatment of lipid disorders.

In some methods of treatment of lipid disorders, in the broadest sense, it may be desirable to have available a physically applicable or implantable predetermined solid form of material containing the composition of the invention. In such embodiments, the compositions of the present invention may be combined with a solid carrier that is bio-acceptable and suitably shaped for its use.

For oral administration, the compounds may be formulated readily by combining these compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. For example, the compounds of the invention may be incorporated into a solid pill or may in the form of a liquid dispersion or suspension. In general, therefore, the compositions of the present invention preferably comprise compounds of Formula I and a suitable, non-toxic, physiologically acceptable carrier. A variety of non-toxic physiologically acceptable carriers may be used in forming these compositions, and it is generally preferred that these compositions be of physiologic salinity.

Pharmaceutical preparations for oral use may be obtained by adding a solid excipient, optionally grinding the resulting mixture, and processing the mixture of granules, after adding suitable auxiliaries, if desired, to obtain tablets or dragee cores. For buccal administration, the compositions can take the form of, e.g., tablets or lozenges formulated in a conventional manner.

Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents may be added, such as, but not limited to, the cross-linked polyvinyl pyrrolidone, agar, or alginic acid or a salt thereof such as sodium alginate.

A formulation of a pharmaceutical composition for oral administration may be prepared in the form of a discrete solid dose unit including, but not limited to, a tablet, a hard or soft capsule, a cachet, a troche, or a lozenge, each containing a predetermined amount of the active ingredient. Other formulations suitable for oral administration may include, but are not limited to, a powdered or granular formulation, an aqueous or oily suspension, an aqueous or oily solution, or an emulsion. As used herein, an "oily" liquid comprises a carbon-containing liquid molecule that exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture.

Pharmaceutically acceptable excipients used in the manufacture of tablets include, but are not limited to, inert diluents, granulating and disintegrating agents, binding agents, and lubricating agents. Dispersing agents include, but are not limited to, potato starch and sodium starch glycolate. Surface active agents include, but are not limited to, sodium lauryl sulphate. Diluents include, but are not limited to, calcium carbonate, sodium carbonate, lactose, microcrystalline cellulose, calcium phosphate, calcium hydrogen phosphate, and sodium phosphate. Granulating and disintegrating agents include, but are not limited to, corn starch and alginic acid. Binding agents include, but are not limited to, gelatin, acacia, pre-gelatinized maize starch, polyvinylpyrrolidone, and hydroxypropyl methylcellulose. Lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.)

Hard capsules comprising the active compound may be made using a physiologically degradable composition, such as gelatin. Such hard capsules comprise the active ingredient, and may further comprise additional ingredients including, for example, an inert solid diluent such as calcium carbonate, calcium phosphate, or kaolin. Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition used in the practice of the invention that are suitable for oral administration may be prepared, packaged, and sold either in liquid form or in the form of a dry product intended for reconstitution with water or another suitable vehicle prior to use. Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropyl methylcellulose. Dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Emulsifying agents may include, but are not limited to, lecithin and acacia. Preservatives include, but are not limited to, methyl, ethyl, or n-propyl para-hydroxybenzoates, ascorbic acid, and sorbic acid. Sweetening agents include, for example, glycerol, propylene glycol, sorbitol, sucrose, and saccharin. Thickening agents for oily suspensions include, for example, beeswax, hard paraffin, and cetyl alcohol.

Powdered and granular formulations of a pharmaceutical preparation used in the practice of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

Dragee cores may be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which may be used orally include, but are not limited to, push-fit capsules made of gelatin, as well as soft, sealed capsules made of gelatin and a plasticizer, such as glycerol or sorbitol. The push-fit capsules may contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of, e.g., tablets or lozenges formulated in a conventional manner.

A pharmaceutical composition used in the practice of the invention may also be prepared in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

In some embodiments, the composition is formulated with a coating. Methods for impregnating or coating a material with a chemical composition are known in the art, and include, but are not limited to methods of depositing or binding a chemical composition onto a surface, methods of incorporating a chemical composition into the structure of a material during the synthesis of the material (e.g. such as with a physiologically degradable material), and methods of absorbing an aqueous or oily solution or suspension into an absorbent material, with or without subsequent drying.

The formulations of the pharmaceutical compositions described herein may be prepared by any method known or hereafter developed in the art of pharmacology. In embodiments, such preparatory methods include the step of bringing the active ingredient into association with a carrier or one or more other accessory ingredients, and then, if necessary or desirable, shaping or packaging the product into a desired single- or multi-dose unit.

In some embodiments, the pharmaceutical composition may be prepared as a single unit dose, or as a plurality of single unit doses. As used herein, a "unit dose" is discrete amount of the pharmaceutical composition comprising a predetermined amount of the active ingredient. In some embodiments, in a unit dose, the amount of the active ingredient is generally equal to the dosage of the active ingredient that would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition used in the practice of the invention will vary, depending upon the identity, size, and condition of the subject treated and further depending upon the route by which the composition is to be administered.

Pharmaceutical compositions of the compounds also can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

In some embodiments, the composition may be administered by vaginal or perivaginal administration. Vaginal or perivaginal dosage forms may include vaginal suppositories, creams, ointments, liquid formulations, pessaries, tampons, gels, pastes, foams or sprays. In embodiments, the suppository, cream, ointment, liquid formulation, pessary, tampon, gel, paste, foam or spray for vaginal or perivaginal delivery may comprise a therapeutically effective amount of the selected active agent and one or more conventional nontoxic carriers suitable for vaginal or perivaginal drug administration. In embodiments, the vaginal or perivaginal forms of the present invention may be manufactured using conventional processes as disclosed in Remington: The Science and Practice of Pharmacy, supra (see also drug formulations as adapted in U.S. Pat. Nos. 6,515,198; 6,500,822; 6,417,186; 6,416,779; 6,376,500; 6,355,641; 6,258,819; 6,172,062; and 6,086,909). In some embodiments, the vaginal or perivaginal dosage unit may be fabricated to disintegrate rapidly or over a period of several hours. In some embodiments, the time period for complete disintegration may be in the range of from about 10 minutes to about 6 hours, e.g., less than about 3 hours.

In some embodiments, the composition may be administered intranasally or by inhalation. Compositions for intranasal administration may be liquid formulations for administration as a spray or in the form of drops, although powder formulations for intranasal administration, e.g., insufflations, nasal gels, creams, pastes or ointments or other suitable formulators can be used. For liquid formulations, the compounds of embodiment herein may be formulated into a solution, e.g., water or isotonic saline, buffered or unbuffered, or as a suspension. In certain embodiments, such solutions or suspensions may be isotonic relative to nasal secretions and of about the same pH, ranging e.g., from about pH 4.0 to about pH 7.4 or, from about pH 6.0 to about pH 7.0. Buffers should be physiologically compatible and include, for example, phosphate buffers. Furthermore, various devices are available in the art for the generation of drops, droplets and sprays, including droppers, squeeze bottles, and manually and electrically powered intranasal pump dispensers. Compositions containing intranasal carriers may also include nasal gels, creams, pastes or ointments with a viscosity of, e.g., from about 10 to about 6,500 cps, or greater, depending on the desired sustained contact with the nasal mucosal surfaces. Such carrier viscous formulations may be based upon, for example, alkylcelluloses and/or other biocompatible carriers of high viscosity well known to the art (see e.g., Remington: The Science and Practice of Pharmacy, supra). Other ingredients, such as preservatives, colorants, lubricating or viscous mineral or vegetable oils, perfumes, natural or synthetic plant extracts such as aromatic oils, and humectants and viscosity enhancers such as, e.g., glycerol, can also be included to provide additional viscosity, moisture retention and a pleasant texture and odor for the formulation. Formulations for inhalation may be prepared as an aerosol, either a solution aerosol in which the active agent is solubilized in a carrier (e.g., propellant) or a dispersion aerosol in which the active agent is suspended or dispersed throughout a carrier and an optional solvent. In embodiments, non-aerosol formulations for inhalation may take the form of a liquid, typically an aqueous suspension, although aqueous solutions may be used as well. In further embodiments, the carrier may a sodium chloride solution having a concentration such that the formulation is isotonic relative to normal body fluid. In embodiments, the liquid formulations may contain water and/or excipients including an antimicrobial preservative (e.g., benzalkonium chloride, benzethonium chloride, chlorobutanol, phenylethyl alcohol, thimerosal and combinations thereof), a buffering agent (e.g., citric acid, potassium metaphosphate, potassium phosphate, sodium acetate, sodium citrate, and combinations thereof), a surfactant (e.g., polysorbate 80, sodium lauryl sulfate, sorbitan monopalmitate and combinations thereof), and/or a suspending agent (e.g., agar, bentonite, microcrystalline cellulose, sodium carboxymethylcellulose, hydroxypropyl methylcellulose, tragacanth, veegum and combinations thereof). In further embodiments, non-aerosol formulations for inhalation may comprise dry powder formulations, particularly insufflations in which the powder has an average particle size of from about 0.1 µm to about 50 µm, e.g., from about 1 µm to about 25 µm.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

In some embodiments, the compositions may be administered using topical administration. Topical formulations can be in any form suitable for application to the body surface, and may comprise, for example, an ointment, cream, gel, lotion, solution, paste or the like, and/or may be prepared so as to contain liposomes, micelles, and/or microspheres. In certain embodiments, topical formulations herein may be ointments, creams or gels.

In some embodiments, the compositions may be administered using transdermal administration. Transdermal administration involves the delivery of pharmaceutical compounds via percutaneous passage of the compound into the systemic circulation of the patient. Topical administration can also involve the use of transdermal administration such as transdermal patches or iontophoresis devices. Other components can be incorporated into the transdermal patches as well. For example, compositions and/or transdermal patches may be formulated with one or more preservatives or bacteriostatic agents including, but not limited to, methyl hydroxybenzoate, propyl hydroxybenzoate, chlorocresol, benzalkonium chloride, and the like. Dosage forms for topical administration of the compounds and compositions may include creams, sprays, lotions, gels, ointments, eye drops, nose drops, ear drops, and the like. In some embodiments, the composition may be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water and sorbitol solution. In addition, in certain embodiments, the compositions may contain polyethylene glycol 400. Such ingredients may be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g., gauze, can be impregnated with the compositions in solution, lotion, cream, ointment or other such form can also be used for topical application.

In some embodiments, the composition may also be applied topically using a transdermal system, such as, without limitation, one of an acrylic-based polymer adhesive with a resinous crosslinking agent impregnated with the composition and laminated to an impermeable backing. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are separate and distinct layers, with the adhesive underlying the reservoir that, in this case, may be either a polymeric matrix as described above, or be a liquid or hydrogel reservoir, or take some other form.

In transdermal administration, the compounds of the present invention, for example, can be applied to a plaster, or can be applied by transdermal, therapeutic systems that are consequently supplied to the organism.

In some embodiments, the composition may be administered using intravesical administration. The term "intravesical administration" is used herein in its conventional sense to mean delivery of a drug directly into the bladder. Suitable methods for intravesical administration can be found, for example, in U.S. Pat. Nos. 6,207,180 and 6,039,967.

With regard to transurethal administration, the composition may comprise a urethral dosage form containing the active agent and one or more selected carriers or excipients, such as water, silicone, waxes, petroleum jelly, polyethylene glycol ("PEG"), propylene glycol ("PG"), liposomes, sugars such as mannitol and lactose, and/or a variety of other materials. A transurethral permeation enhancer can be included in the dosage from. Examples of suitable permeation enhancers include dimethylsulfoxide ("DMSO"), dimethyl formamide ("DMF"), N,N-dimethylacetamide ("DMA"), decylmethylsulfoxide ("C10 MSO"), polyethylene glycol monolaurate ("PEGML"), glycerol monolaurate, lecithin, the 1-substituted azacycloheptan-2-ones, particularly 1-n-dodecyl-cyclazacycloheptan-2-one (available under the trademark Azone™ from Nelson Research & Development Co., Irvine, Calif.), SEPA™ (available from Macrochem Co., Lexington, Mass.), surfactants as discussed above, including, for example, Tergitol™, Nonoxynol-9™ and TWEEN-80™, and lower alkanols such as ethanol.

Transmucosal administration may be carried out using any type of formulation or dosage unit suitable for application to mucosal tissue. For example, the selected active agent may be administered to the buccal mucosa in an adhesive tablet or patch, sublingually administered by placing a solid dosage form under the tongue, lingually administered by placing a solid dosage form on the tongue, administered nasally as droplets or a nasal spray, administered by inhalation of an aerosol formulation, a non-aerosol liquid formulation, or a dry powder, placed within or near the rectum ("transrectal" formulations), or administered to the urethra as a suppository, ointment, or the like.

Transrectal dosage forms may include rectal suppositories, creams, ointments, and liquid formulations (enemas). The suppository, cream, ointment or liquid formulation for transrectal delivery comprises a therapeutically effective amount of the selected active agent and one or more conventional nontoxic carriers suitable for transrectal drug administration. The transrectal dosage forms of the present invention can be manufactured using conventional processes. The transrectal dosage unit can be fabricated to disintegrate rapidly or over a period of several hours. The time period for complete disintegration may be in the range of from about 10 minutes to about 6 hours, e.g., less than about 3 hours.

The compounds of the present invention may also be formulated in rectal compositions such as suppositories or retention enemas, e.g., containing conventional suppository bases such as cocoa butter or other glycerides.

In addition to the formulations described previously, the compounds of the present invention can also be formulated as a depot preparation. Such long acting formulations can be administered by implantation (for example subcutaneously or intramuscularly) or by intramuscular injection.

In some embodiments, depot injections may be administered at about 1 to about 6 months or longer intervals. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions that are useful in the methods used in the practice of the invention may be prepared in formulations suitable for oral, rectal, intracisternal, intravaginal, intraperitoneal or local, or another route of administration. Other contemplated formulations include projected nanoparticles, liposomal preparations, resealed erythrocytes containing the active ingredient, and immunologically-based formulations.

The formulations of the pharmaceutical compositions described herein may be prepared by any method known or hereafter developed in the art of pharmacology. In embodiments, such preparatory methods include the step of bringing the active ingredient into association with a carrier or one or more other accessory ingredients, and then, if necessary or desirable, shaping or packaging the product into a desired single- or multi-dose unit. Controlled- or sustained-release formulations of a pharmaceutical composition used in the practice of the invention may be made using conventional technology.

In certain embodiments, the formulations of the present invention can be, but are not limited to, short-term release or rapid-offset release, as well as controlled release, for example, sustained release, delayed release and pulsatile release formulations. As used herein, the term "short-term release" or "rapid-offset release" is used in its conventional sense to refer to a drug formulation that provides for release of the drug immediately after drug administration. In some embodiments, short-term or rapid-offset may refer to any period of time up to and including about 8 hours, about 7 hours, about 6 hours, about 5 hours, about 4 hours, about 3 hours, about 2 hours, about 1 hour, about 40 minutes, about 20 minutes, or about 10 minutes or any combination thereof after drug administration.

In an embodiment, the compositions or compounds of embodiments herein may be administered to a subject, alone or in combination with another pharmaceutical agent, using a sustained release formulation. As used herein, the term "sustained release" is used in its conventional sense to refer to a drug formulation that provides for gradual release of a drug over an extended period of time, and that may, although not necessarily, result in substantially constant blood levels of a drug over an extended time period. The period of time may be as long as a month or more and may be longer than the time required for the release of the same amount of agent administered in bolus form. For sustained release, the compounds may be formulated with a suitable polymer or hydrophobic material that provides sustained release properties to the compounds. As such, the compounds of the invention may be administered in the form of microparticles, for example, by injection or in the form of wafers or discs by implantation.

In an embodiment, the compositions or compounds of embodiments herein may be administered to a subject, alone or in combination with another pharmaceutical agent, using a delayed release formulation. As used herein, the term "delayed release" is used in its conventional sense to refer to a drug formulation that provides for an initial release of the drug after some delay following drug administration and that may, although not necessarily, include a delay of from about 10 minutes up to about 12 hours.

In an embodiment, the compositions or compounds of embodiments herein may be administered to a subject, alone or in combination with another pharmaceutical agent, using a pulsatile release formulation. As used herein, the term "pulsatile release" is used in its conventional sense to refer to a drug formulation that provides release of the drug in such a way as to produce pulsed plasma profiles of the drug after drug administration.

In embodiments, the formulations of embodiments described herein may comprise additional ingredients. As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents; demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

In another aspect, the compound of Formula I may be formulated using one or more pharmaceutically acceptable excipients selected from starch, sugar, cellulose, diluent, granulating agent, lubricant, binder, disintegrating agent, wetting agent, emulsifier, coloring agent, release agent, coating agent, sweetening agent, flavoring agent, perfuming agent, preservative, antioxidant, plasticizer, gelling agent, thickener, hardener, setting agent, suspending agent, surfactant, humectant, carrier, stabilizer, or any combinations thereof.

In some embodiments, the disintegrant component comprises one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

In some embodiments, the diluent component comprises one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

In some embodiments, the optional lubricant component, when present, comprises one or more of stearic acid, metallic stearate, sodium stearylfumarate, fatty acid, fatty alcohol, fatty acid ester, glycerylbehenate, mineral oil, vegetable oil, paraffin, leucine, silica, silicic acid, talc, propylene glycol fatty acid ester, polyethoxylated castor oil, polyethylene glycol, polypropylene glycol, polyalkylene glycol, polyoxyethylene-glycerol fatty ester, polyoxyethylene fatty alcohol ether, polyethoxylated sterol, polyethoxylated castor oil, polyethoxylated vegetable oil, or sodium chloride.

Embodiments herein also include a kit comprising at least one of the components described above for performing a method of the invention. According to one embodiment, a kit may comprise a carrier, a compound having a structure of Formula I, and a dispenser. In some embodiments, the dispenser may be selected from a dropper, pipette tips, wipes, spray, Q-tips, needle syringe. In some embodiments, the kit aids in the treatment of lipid disorders.

The kit may be "single use only," in which case a single kit is sufficient for the treatment of the disease or disorder. Alternatively, the kit may comprise one or more combination of molecules, compounds, factors, agents, or the like mentioned above and may comprise multiple single-use containers. In some embodiments, the kit is configured in manner that minimizes steps or negates the need for dilutions, weighing or measurements to be performed by a care taker (i.e. doctor, nurse, surgeon, etc) or a subject. In some embodiments, a container may be any sealed or re-sealable vessel suitable for carrying a quantity of treatment. Examples include, but are not limited to screw cap vials, push cap vials, break-seal-to-open vials or syringes. In some embodiments, the kits may comprise the stated items or combinations of items, packaging materials, instructions, and combinations thereof.

In another embodiment, a kit comprises a dispenser, composition, or other components to treat the disease or disorder. Optionally, the kit may comprise instructions for composition preparation and other accessories including, but not limited to, a delivery vehicle and carriers for the treatment of the disease or disorder. In embodiments, the kit may include printed instructions for administering the composition to a subject undergoing treatment according to a dosing regimen. In some embodiments, the dosing regimen contains a period during which preferred dosages are adjusted to deliver an amount of said compound sufficient to maintain a target local tissue level or whole blood. In other embodiments, the kit may comprise the composition in dosage units suitable for use in the methods described herein.

In embodiments, the pharmaceutical compositions of the invention may be dispensed to the subject under treatment with the help of an applicator. The applicator to be used may depend on the specific medical condition being treated, amount and physical status of the pharmaceutical composition, and choice of those skilled in the art.

This invention and embodiments illustrating the method and materials used may be further understood by reference to the following non-limiting examples.

Example 1

A study was conducted to evaluate toxicity in monkeys with HPI-363 at doses of 0.05 to 5 mg/kg. The compound was administered as a slow IV push over 20 to 30 seconds. Six animals (3 males and 3 females) approximately 2 years old and weighing 2.1-2.5 kilograms were dosed once daily for 14 days. Blood chemistry was collected on Days 1-15. Evaluation of serum chemistry revealed a dose dependent effect on cholesterol and triglycerides. A reduction of 27%-40% in levels of cholesterol and triglycerides respectively from predose was observed over 15 days. The lipid-lowering effect occurred within a 12 hr-period. There was a transient rise of liver enzymes in the animals which normalized within the 15 days of the study.

Example 2

Male Sprague-Dawley (SD, Harlan Laboratories) rats (210-220 g at initiation of experiments) and genetically obese Zucker (fa/fa) (ZF, Harlan Laboratories) rats (210-220 g at initiation of experiments) were housed individually under a 12 h:12 h light:dark schedule (lights on at 7:00 AM). All compound administration, animal and food weighing were performed between noon and 1 PM (during the light phase of the animals' circadian illumination schedule). Each rat was provided standard rat chow and water ad libitum throughout the experiments.

Each animal received either 1 mg/kg HPI-363 dissolved in saline IV (Treated) or saline (Vehicle or Untreated) for ten consecutive days followed by daily injections of saline for ten additional days. At the start of the experiment, each animal was weighed and single-housed with rat chow and water, with subsequent weighing occurring at 24 hr increments for 20 days. For food intake, 100 g of rat chow was placed in each animal's hopper and leftover chow in the hopper was collected and weighed every 24 hr for 20 days at the time of animal weighing. Chow was then replenished to 100 g each day. As a monitor of the general health of the animals, rats were observed twice daily. No deviations from normal affect were noted.

Figure 3:
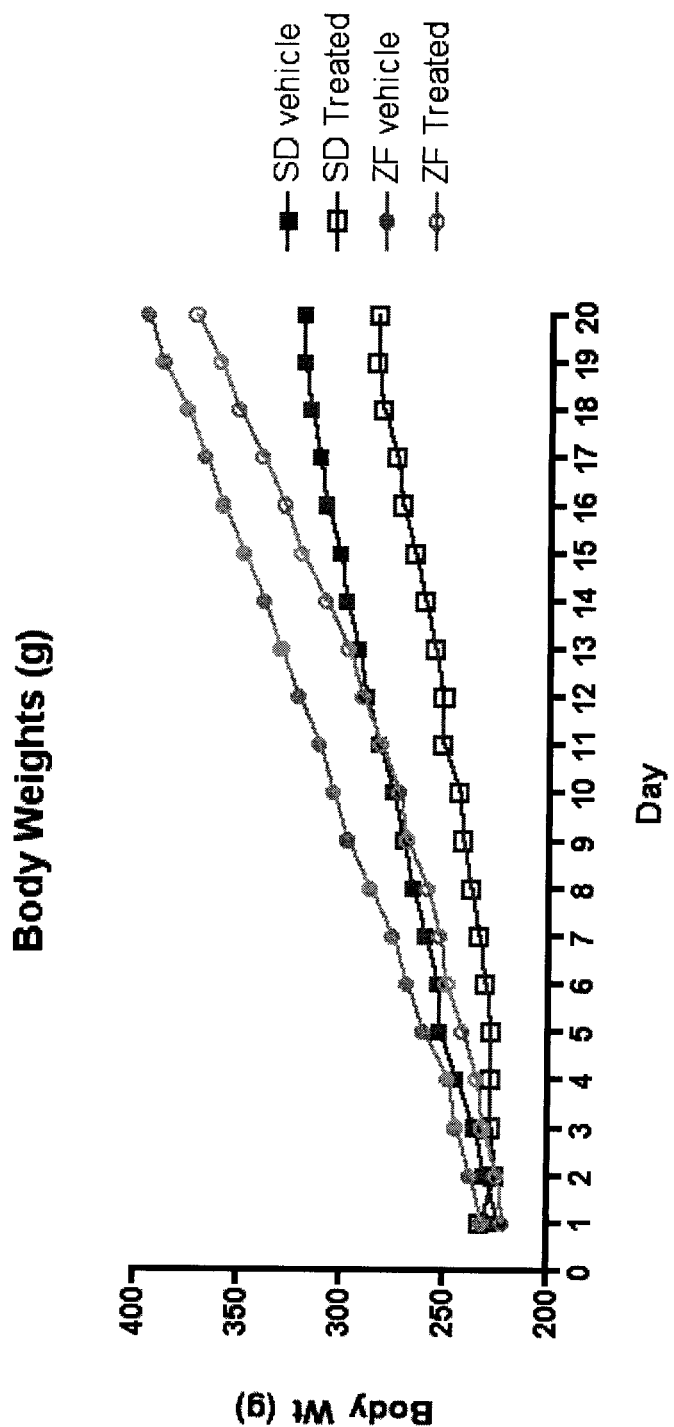
FIG. 3 illustrates the daily weights for normal (Sprague-Dawley, SD) and fatty (Zucker, ZF) rats treated with 1 mg/kg of HPI-363 daily for days 1-10 then saline for days 11-20 (Treated, N=2), or with saline days 1-10 and 11-20 (vehicle, N=1).

The time course body weights of SD and ZF rats for 20 days with IV injection of either saline (vehicle) or HPI-363 (Treated) are shown in FIG. 3. Administration of HPI-363 resulted in an inhibition of weight gain in both SD and ZF rats (Days 1-10), which is maintained after cessation of compound (Days 11-20).

The data for weight change and food consumption over the course of the experiments for both SD and ZF rats are compiled in Table 1. Significant inhibition of weight increases were seen with administration of HPI-363 in both types of animals through Days 1-10, which appears to correlate with decreased food intake. After cessation of HPI-363 administration (Days 11-20), both weight gain and food consumption returned to normal for both types of rats, however, the difference in weight gain between SD and ZF rats was maintained.

TABLE 1

| Group | Avg. Wt. Change (g) Days 1-10 | SD | Food Consumption. (g) Days 1-10 | SD | Avg. Wt. Change (g) Days 11-20 | SD | Food Consumption. (g) Days 11-20 | SD |
|---|---|---|---|---|---|---|---|---|
| SD Untreated | 46.4 | 7.1 | 223.1 | 0.4 | 39.2 | 2.5 | 231.8 | 9.3 |
| SD Treated | 17.4 | 11.4 | 148.5 | 12.1 | 40.0 | 9.7 | 222.0 | 9.0 |
| ZF Untreated | 77.8 | 6.7 | 313.8 | 14.6 | 86.0 | 2.7 | 371.1 | 12.9 |
| ZF Treated | 54.6 | 5.7 | 252.7 | 17.4 | 88.5 | 4.9 | 402.0 | 28.4 |

Although the present invention has been described in considerable detail with reference to certain preferred embodiments thereof, other versions are possible. Therefore the spirit and scope of the appended claims should not be limited to the description and the preferred versions contained within this specification.

The invention claimed is:

1. A pharmaceutical composition comprising an effective amount of a compound of formula

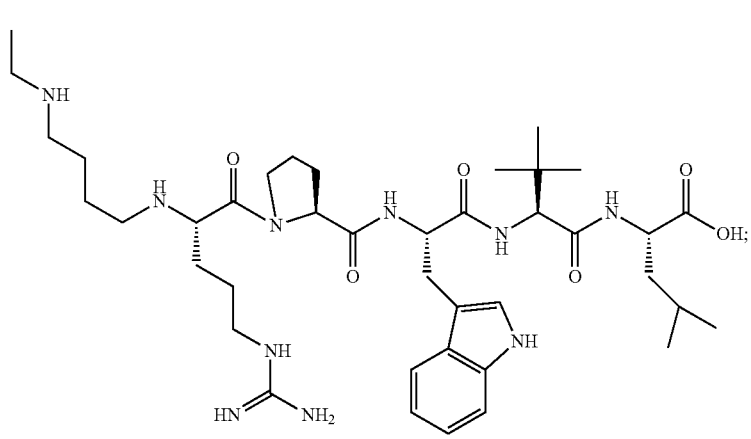

HPI-501 or a pharmaceutically acceptable salt, hydrate, or solvate thereof; and a pharmaceutically acceptable excipient.

2. A compound having the formula:

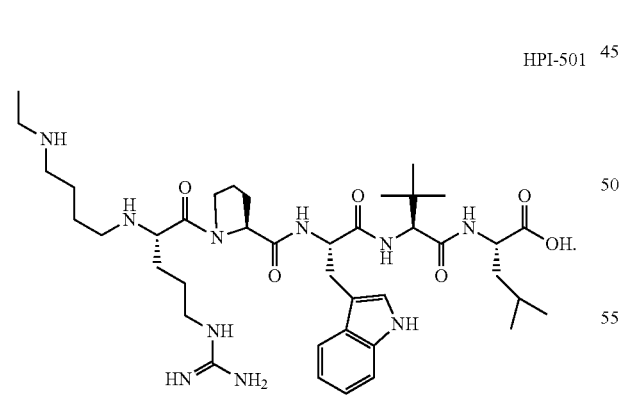

HPI-501

3. A compound having the formula:

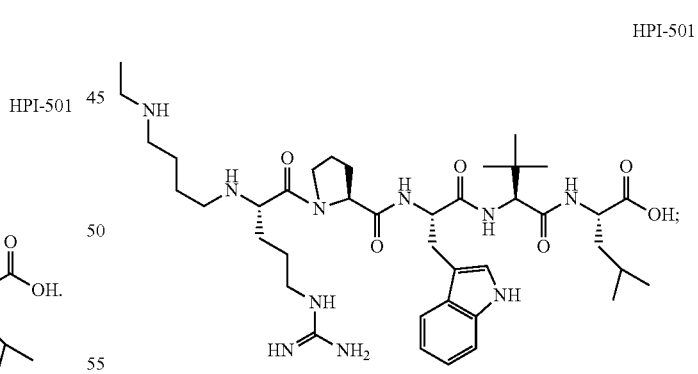

HPI-501 or pharmaceutically acceptable salt, hydrate, or solvate thereof.

* * * * *